US008088743B2

(12) United States Patent
Washburn et al.

(10) Patent No.: US 8,088,743 B2
(45) Date of Patent: *Jan. 3, 2012

(54) METHODS FOR TREATING OBESITY EMPLOYING AN SGLT2 INHIBITOR

(75) Inventors: William N. Washburn, Titusville, NJ (US); Jean Whaley, Bedminster, NJ (US); Mario Maldonado, Basel (CH); James F. List, Princeton, NJ (US); Frederick T. Fiedorek, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 727 days.

This patent is subject to a terminal disclaimer.

(21) Appl. No.: 12/053,508

(22) Filed: Mar. 21, 2008

(65) Prior Publication Data

US 2008/0234367 A1    Sep. 25, 2008

Related U.S. Application Data

(60) Provisional application No. 60/896,291, filed on Mar. 22, 2007, provisional application No. 60/981,361, filed on Oct. 19, 2007, provisional application No. 61/018,918, filed on Jan. 4, 2008.

(51) Int. Cl.
*A61K 31/70* (2006.01)

(52) U.S. Cl. ............... 514/23; 514/25; 514/27; 514/909

(58) Field of Classification Search ............... 514/23, 514/25, 27, 909
See application file for complete search history.

(56) References Cited

U.S. PATENT DOCUMENTS

| 6,414,126 | B1 * | 7/2002 | Ellsworth et al. | 536/17.2 |
| 6,515,117 | B2 * | 2/2003 | Ellsworth et al. | 536/17.2 |
| 6,936,590 | B2 * | 8/2005 | Washburn et al. | 514/25 |
| 6,972,283 | B2 * | 12/2005 | Fujikura et al. | 514/27 |
| 7,202,350 | B2 * | 4/2007 | Imamura et al. | 536/1.11 |
| 7,589,193 | B2 * | 9/2009 | Washburn et al. | 536/122 |
| 2004/0138439 | A1 | 7/2004 | Deshpande et al. | |
| 2008/0004336 | A1 | 1/2008 | Gougoutas et al. | |
| 2008/0234366 | A1 | 9/2008 | Bindra et al. | |

FOREIGN PATENT DOCUMENTS

| EP | 1 270 584 A | 1/2003 |
| WO | WO 01/27128 A | 4/2001 |
| WO | WO 03/099836 A1 | 12/2003 |
| WO | WO 2005012242 A2 * | 2/2005 |
| WO | WO 2006/034489 A2 | 3/2006 |
| WO | WO 2008/002824 | 1/2008 |

OTHER PUBLICATIONS

Devenny et al., "The Effect of Dapagliflozin, a Highly Selective SGLT-2 Inhibitor on Body Weight in Diet-Induced Obese Rats," Obesity, vol. 15, No. Suppl. 9, (2007).
Handlon A. L.: "Sodium glucose co-transporter 2 (SGLT2) inhibitors as potential antidiabetic agents," Expert Opinion on Therapeutic Patients, Informa HealthCare, GB, vol. 15, No. 11, Jan. 1, 2005, pp. 1531-1540.
James F. List et al.: "Dapagliflozin-Induced glucosuria Is Accompanied by Weight Loss in Type 2 diabetes Patients," supported by Bristol-Myers Squibb and AstraZeneca, Bristol-Myers Squibb, Princeton and Hopewell, NJ, HEalth Sciences Centre Diabetes research Centre Winnpeg Manitoba, Candad, Centro de Investigaticion Cardiomtabolica Aguascalientes, Mexico, #461-P.
Songping Han, Ph.D. et al.: "Dapagliflozin, a selective SGLT2 inhibitor, improves glucose homeostasis in normal and diabetic rats," Diabetes Publish Ahead of Print, published online Mar. 20, 2008.
James F. List et al.: "Sodium-Glucose Co-Transport Inhibition With Dapagliflozin in Type 2 Diabetes Mellitus," Diabetes Care Publish Ahead of Print, published online Dec. 29, 2008; Clinical trial reg. No. NCT00263276, clinical trials.gov; Submitted Oct. 15, 2008 and accepted Dec. 22, 2008.
Jurczak MJ et al.: "SGLT2 knockout improves glucose tolerance in lean and fat-fed mice," Departments of Internal Medicine and Cellular and Molecular Physiology, Howard Hughes Medical Institute, Yale University School of Medicine, New Haven, CT and Metabolic Diseases Biology, Bristol-Myers Squibb Research and Development, Princeton, NJ., Jun. 5, 2009.
Whaley J. et al.: "Dapagliflozin, A Selective SGLT2 Inhibitor, Improves Glucose Homeostasis in Normal and Diabetic Rats," supported by Bristol-Myers Squibb and AstraZeneca, Bristol-Myers Squbb, Princeton, NJ, current Affiliation: Novartis Institutes for Biomedical Research, Cambridge, MA; current Affiliation: Pfizer global Research and Development, Ann Arbor, MI., Oct. 22, 2008.

* cited by examiner

*Primary Examiner* — Kevin E Weddington
(74) *Attorney, Agent, or Firm* — McDonnell Boehnen Hulbert & Berghoff LLP

(57) ABSTRACT

Methods are provided for treating obesity or causing weight loss in a mammalian subject or patient, wherein a therapeutically effective amount of an SGLT2 inhibitor alone or optionally in combination with another anti-obesity agent, is administered to a mammalian subject or patient. In addition, a pharmaceutical composition is provided which comprises an SGLT2 inhibitor, alone or in combination with another anti-obesity agent, and a pharmaceutically acceptable carrier thereof.

7 Claims, 5 Drawing Sheets

Indirect comparison of GSK 869,682 and Dapagliflozin-PGS

Weight loss in diet-induced obese rats treated with Dapagliflozin-PGS

BMS-655956 DIO Rat Study
Percent Change in Body Weight

METHODS FOR TREATING OBESITY EMPLOYING AN SGLT2 INHIBITOR

This application claims priority to U.S. Provisional Ser. No. 60/896,291, filed on Mar. 22, 2007, U.S. Provisional Ser. No. 60/981,361, filed on Oct. 19, 2007, and U.S. Provisional Ser. No. 61/018,918, filed Jan. 4, 2008

FIELD OF THE INVENTION

The present invention provides a method for treating obesity or causing weight loss in a mammal employing an SGLT2 inhibitor alone or in combination with another anti-obesity agent, and to a pharmaceutical composition for use in such method.

BACKGROUND OF THE INVENTION

Hyperglycemia, that is, elevated plasma glucose, is a hallmark of diabetes. Plasma glucose is normally filtered in the kidney in the glomerulus and actively reabsorbed in the proximal tubule. Sodium-dependent glucose transporter SGLT2 appears to be the major transporter responsible for the reuptake of glucose at this site. The SGLT specific inhibitor phlorizin, and closely related analogs, inhibit this reuptake process in diabetic rodents and dogs, resulting in normalization of plasma glucose levels by promoting glucose excretion without hypoglycemic side effects. Long term (6 month) treatment of Zucker diabetic rats with an SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity and delaying the development of diabetic complications.

Ninety percent of glucose reuptake in the kidney occurs in the epithelial cells of the early S1 segment of the renal cortical proximal tubule, and SGLT2 is likely to be the major transporter responsible for this reuptake. SGLT2 is a 672 amino acid protein containing 14 membrane-spanning segments that is predominantly expressed in the early S1 segment of the renal proximal tubules. The substrate specificity, sodium-dependence, and localization of SGLT2 are consistent with the properties of the high capacity, low affinity, sodium-dependent glucose transporter previously characterized in human cortical kidney proximal tubules. In addition, hybrid depletion studies implicate SGLT2 as the predominant $Na^+$/glucose cotransporter in the S1 segment of the proximal tubule, since virtually all sodium-dependent glucose transport activity encoded in mRNA from rat kidney cortex is inhibited by an antisense oligonucleotide specific to rat SGLT2. SGLT2 is a candidate gene for some forms of familial glucosuria, a genetic abnormality in which renal glucose reabsorption is impaired to varying degrees. None of these syndromes investigated to date map to the SGLT2 locus on chromosome 16. However, the studies of highly homologous rodent SGLTs strongly implicate SGLT2 as the major renal sodium-dependent transporter of glucose and suggest that the glucosuria locus that has been mapped encodes an SGLT2 regulator. Inhibition of SGLT2 would be predicted to reduce plasma glucose levels via enhanced glucose excretion in diabetic patients.

SGLT1, another sodium-dependent glucose cotransporter that is 60% identical to SGLT2 at the amino acid level, is expressed in the small intestine and in the more distal S3 segment of the renal proximal tubule. Despite their sequence similarities, human SGLT1 and SGLT2 are biochemically distinguishable. For SGLT1, the molar ratio of $Na^+$ to glucose transporter is 2:1, whereas for SGLT2, the ratio is 1:1. The $K_m$ for $Na^+$ is 32 and 250-300 mM for SGLT1 and SGLT2, respectively. $K_m$ values for uptake of glucose and the nonmetabolizable glucose analog α-methyl-D-glucopyranoside (AMG) are similar for SGLT1 and SGLT2, i.e. 0.8 and 1.6 mM (glucose) and 0.4 and 1.6 mM (AMG) for SGLT1 and SGLT2 transporters, respectively. However, the two transporters vary in their substrate specificities for sugars such as galactose, which is a substrate for SGLT1 only.

Administration of phlorizin, a specific inhibitor of SGLT activity, provided proof of concept in vivo by promoting glucose excretion, lowering fasting and fed plasma glucose, and promoting glucose utilization without hypoglycemic side effects in several diabetic rodent models and in one canine diabetes model. No adverse effects on plasma ion balance, renal function or renal morphology have been observed as a consequence of phlorizin treatment for as long as two weeks. In addition, no hypoglycemic or other adverse effects have been observed when phlorizin is administered to normal animals, despite the presence of glycosuria. Administration of an inhibitor of renal SGLTs for a 6-month period (Tanabe Seiyaku) was reported to improve fasting and fed plasma glucose, improve insulin secretion and utilization in obese type II diabetes (NIDDM) rat models, and offset the development of nephropathy and neuropathy in the absence of hypoglycemic or renal side effects.

Phlorizin itself is unattractive as an oral drug since it is a nonspecific SGLT1/SGLT2 inhibitor that is hydrolyzed in the gut to its aglycone phloretin, which is a potent inhibitor of facilitated glucose transporter. Concurrent inhibition of facilitative glucose transporters (GLUTs) is undesirable since such inhibitors would be predicted to exacerbate peripheral insulin resistance as well as promote hypoglycemia in the CNS. Inhibition of SGLT1 could also have serious adverse consequences as is illustrated by the hereditary syndrome glucose/galactose malabsorption (GGM), in which mutations in the SGLT1 cotransporter result in impaired glucose uptake in the intestine, and life-threatening diarrhea and dehydration. The biochemical differences between SGLT2 and SGLT1, as well as the degree of sequence divergence between them, allow for identification of selective SGLT2 inhibitors.

The familial glycosuria syndromes are conditions in which intestinal glucose transport, and renal transport of other ions and amino acids, are normal. Familial glycosuria patients appear to develop normally, have normal plasma glucose levels, and appear to suffer no major health deficits as a consequence of their disorder, despite sometimes quite high (110-114 g/daily) levels of glucose excreted. The major symptoms evident in these patients include polyphagia, polyuria and polydipsia, and the kidneys appear to be normal in structure and function. Thus, from the evidence available thus far, defects in renal reuptake of glucose appear to have minimal long term negative consequences in otherwise normal individuals.

BRIEF DESCRIPTION OF THE INVENTION

In accordance with the present invention, a method is provided for treating obesity in a mammalian subject or patient, including a human subject or patient, which includes the step of administering to a mammalian subject or patient in need of such treatment a therapeutically effective (weight-reducing) amount of an SGLT2 inhibitor. In certain embodiments, the inventive methods for treating obesity in a mammalian subject or patient, including a human subject or patient, comprise administering a therapeutically effective amount of dapagliflozin or dapagliflozin propylene glycol hydrate (also referred to as dapagliflozin propylene glycol solvate or dapagliflozin-PGS). In certain embodiments, the present invention provides methods for treating obesity in a mammalian subject or patient, including a human subject or patient, with type II diabetes mellitus comprising administering a therapeutically effective amount of an SGLT2 inhibitor. In certain embodiments, the present invention provides methods for treating obesity in a mammalian subject or patient, including a human subject or patient, with type II diabetes mellitus comprising administering a therapeutically effective amount of dapagliflozin or dapagliflozin-PGS. In one embodiment, the method for treating obesity in a mammalian subject or patient comprises administering to a mammalian subject or patient in need of such treatment a therapeutically effective amount of an SGLT2 inhibitor, for example dapagliflozin or dapagliflozin-PGS, wherein the amount is below the effective amount for treating diabetes. In one embodiment, the method for treating obesity in a mammalian subject or patient, including a human subject or patient, with type II diabetes mellitus comprises administering a therapeutically effective amount of an SGLT2 inhibitor, for example dapagliflozin or dapagliflozin-PGS, wherein the amount is below the effective amount for treating diabetes.

In addition, in accordance with the present invention, a method is provided for promoting, increasing or enhancing glucosuria in a mammalian subject or patient, including a human subject or patient, to effect weight loss, which includes the step of administering to a mammalian subject or patient in need of such treatment a therapeutically effective (glucosuria-enhancing or weight-reducing) amount of an SGLT2 inhibitor. In certain embodiments, the inventive methods for increasing or enhancing glucosuria in a mammalian subject or patient, including a human subject or patient, to effect weight loss comprise administering a therapeutically effective amount of dapagliflozin or dapagliflozin-PGS. In certain embodiments, the present invention provides methods for increasing or enhancing glucosuria in a mammalian subject or patient, including a human subject or patient, with type II diabetes mellitus to effect weight loss comprising administering a therapeutically effective amount of an SGLT2 inhibitor. In certain embodiments, the present invention provides methods for increasing or enhancing glucosuria in a mammalian subject or patient, including a human subject or patient, with type II diabetes mellitus to effect weight loss comprising administering a therapeutically effective amount of dapagliflozin or dapagliflozin-PGS. In one embodiment, the method for increasing or enhancing glucosuria in a mammalian subject or patient comprises administering to a mammalian subject or patient in need of such treatment a therapeutically effective amount of an SGLT2 inhibitor, for example dapagliflozin or dapagliflozin-PGS, wherein the amount is below the effective amount for treating diabetes. In one embodiment, the method for increasing or enhancing glucosuria in a mammalian subject or patient, including a human subject or patient, with type II diabetes mellitus comprises administering a therapeutically effective amount of an SGLT2 inhibitor, for example dapagliflozin or dapagliflozin-PGS, wherein the amount is below the effective amount for treating diabetes.

In addition, in accordance with the invention, a method for causing weight loss in a mammalian subject or patient, including a human subject or patient, who may or may not be characterized as obese is provided, which includes the step of administering to a mammalian subject or patient in need of treatment a therapeutically effective (weight-reducing) amount of an SGLT2 inhibitor. In certain embodiments, the inventive methods for causing weight loss in a mammalian subject or patient, including a human subject or patient, who may or may not be characterized as obese comprise administering a therapeutically effective amount of dapagliflozin or dapagliflozin-PGS. In certain embodiments, the present invention provides methods for causing weight loss in a mammalian subject or patient, including a human subject or patient, with type II diabetes mellitus who may or may not be characterized as obese comprising administering a therapeutically effective amount of an SGLT2 inhibitor. In certain embodiments, the present invention provides methods for causing weight loss in a mammalian subject or patient, including a human subject or patient, with type II diabetes mellitus who may or may not be characterized as obese comprising administering a therapeutically effective amount of dapagliflozin or dapagliflozin-PGS. In one embodiment, the method for causing weight loss in a mammalian subject or patient, including a human subject or patient, who may or may not be characterized as obese a therapeutically effective amount of an SGLT2 inhibitor, for example dapagliflozin or dapagliflozin-PGS, wherein the amount is below the effective amount for treating diabetes. In one embodiment, the method for causing weight loss in a mammalian subject or patient, including a human subject or patient, with type II diabetes mellitus who may or may not be characterized as obese comprises administering a therapeutically effective amount of an SGLT2 inhibitor, for example dapagliflozin or dapagliflozin-PGS, wherein the amount is below the effective amount for treating diabetes.

In one embodiment, the dosage of SGLT2 inhibitor, including dapagliflozin or dapagliflozin-PGS, employed in any of the methods of the invention for treating a mammalian subject or patient, including a human subject or patient, is the therapeutic amount as prescribed in generally accepted medical procedure for treating diabetes. In another embodiment, the dosage is below the therapeutic amount as prescribed in generally accepted medical procedure for treating diabetes, that is, a sub-therapeutic amount. For example, in one embodiment, the dosage for the SGLT2 inhibitor is from about $\frac{1}{5}$ of the lowest dose normally recommended for treating diabetes up to about $\frac{9}{10}$ of the normally recommended dose for treating diabetes. In one embodiment, the dosage for the SGLT2 inhibitor is below the amount that would cause hypoglycemia.

Thus, in one embodiment of the invention, a method is provided for treating obesity in a mammalian subject or patient, including a human subject or patient, which includes the step of administering to a mammalian subject or patient in need of treatment a therapeutically effective (weight-reducing) amount of an SGLT2 inhibitor which amount is below that prescribed in generally accepted medical practice for treating diabetes. In certain embodiments, the inventive methods for treating obesity in a mammalian subject or patient, including a human subject or patient, comprise administering a therapeutically effective (weight reducing) amount of dapagliflozin or dapagliflozin-propylene glycol hydrate (dapagliflozin-PGS) which amount is below that prescribed in generally accepted medical practice for treating diabetes.

In one embodiment of the invention, a method is provided for treating obesity in a mammalian subject or patient, including a human subject or patient, with type II diabetes which includes the step of administering to the mammalian subject or patient a therapeutically effective (weight-reducing) amount of an SGLT2 inhibitor which amount is below that prescribed in generally accepted medical practice for treating diabetes. In certain embodiments, the inventive methods for treating obesity in a mammalian subject or patient, including a human subject or patient, comprise administering a therapeutically effective (weight reducing) amount of dapagliflozin or dapagliflozin-propylene glycol hydrate (dapagliflozin-PGS) which amount is below that prescribed in generally accepted medical practice for treating diabetes.

In another embodiment of the invention, a method is provided for promoting, increasing or enhancing glucosuria in a mammalian subject or patient, including a human subject or patient, to effect weight loss, which includes the step of administering to a mammalian subject or patient in need of treatment a therapeutically effective (glucosuria-enhancing or weight-reducing) amount of an SGLT2 inhibitor, which amount is below that prescribed in generally accepted medical practice for treating diabetes. In certain embodiments, the inventive methods for promoting, increasing or enhancing glucosuria in a mammalian subject or patient, including a human subject or patient, to effect weight loss in a mammalian subject or patient comprise administering dapagliflozin or dapagliflozin-PGS in an amount below that prescribed in generally accepted medical practice for treating diabetes.

In certain embodiments, the inventive methods for promoting, increasing or enhancing glucosuria in a mammalian subject or patient, including a human subject or patient, with type II diabetes mellitus to effect weight loss comprise administering an SGLT2 inhibitor in an amount below that prescribed in generally accepted medical practice for treating diabetes. In certain embodiments, the inventive methods for promoting, increasing or enhancing glucosuria in a mammalian subject or patient, including a human subject or patient, with type II diabetes mellitus to effect weight loss comprise administering dapagliflozin or dapagliflozin-PGS in an amount below that prescribed in generally accepted medical practice for treating diabetes.

In another embodiment of the invention, a method for causing weight loss in a mammalian subject or patient, including a human subject or patient, who may or may not be characterized as obese, is provided, which includes the step of administering to a mammalian subject or patient in need of treatment a therapeutically effective (weight-reducing) amount of an SGLT2 inhibitor which amount is below that prescribed in generally accepted medical practice for treating diabetes. In certain embodiments, the inventive methods for causing weight loss in a mammalian subject or patient, including a human subject or patient, who may or may not be characterized as obese, comprise administering a therapeutically effective amount of dapagliflozin or dapagliflozin-PGS which amount is below that prescribed in generally accepted medical practice for treating diabetes.

In another embodiment of the invention, a method for causing weight loss in a mammalian subject or patient, including a human subject or patient, with type II diabetes, who may or may not be characterized as obese, is provided, which includes the step of administering to a mammalian subject or patient a therapeutically effective (weight-reducing) amount of an SGLT2 inhibitor which amount is below that prescribed in generally accepted medical practice for treating diabetes. In certain embodiments, the inventive methods for causing weight loss in a mammalian subject or patient, including a human subject or patient, with type II diabetes, who may or may not be characterized as obese, comprise administering a therapeutically effective amount of dapagliflozin or dapagliflozin-PGS which amount is below that prescribed in generally accepted medical practice for treating diabetes.

Still further in accordance with the invention, in any of the described methods, the SGLT2 inhibitor is administered in combination with one or more other anti-obesity agent(s) as defined herein and known in the art. For example, in any of the methods of the invention, dapagliflozin or dapagliflozin-PGS is administered in combination with one or more other anti-obesity agent(s) as defined herein and known in the art. Also, in any of the methods of the invention, the SGLT2 inhibitor is administered in combination with one or more other anti-obesity agent(s), wherein the SGLT2 inhibitor is administered in an amount below that prescribed in generally accepted medical practice for treating diabetes. For example, in any of the methods of the invention, dapagliflozin or dapagliflozin-PGS is administered in combination with one or more other anti-obesity agent(s), wherein the dapagliflozin or dapagliflozin-PGS is administered in an amount below that prescribed in generally accepted medical practice for treating diabetes.

Still further in accordance with the invention, in any of the described methods, the SGLT2 inhibitor is administered in combination with one or more other anti-diabetic agent(s) as defined herein and known in the art. For example, in any of the methods of the invention, dapagliflozin or dapagliflozin-PGS is administered in combination with one or more other anti-diabetic agent(s) as defined herein and known in the art. Also, in any of the methods of the invention, the SGLT2 inhibitor is administered in combination with one or more other anti-diabetic agent(s), wherein the SGLT2 inhibitor is administered in an amount below that prescribed in generally accepted medical practice for treating diabetes. For example, in any of the methods of the invention, dapagliflozin or dapagliflozin-PGS is administered in combination with one or more other anti-diabetic agent(s), wherein the dapagliflozin or dapagliflozin-PGS is administered in an amount below that prescribed in generally accepted medical practice for treating diabetes.

Still further in accordance with the invention, in any of the described methods, the method comprises administering to a mammalian subject or patient a pharmaceutical composition comprising a therapeutically effective amount of an SGLT2 inhibitor and at least one pharmaceutically acceptable carrier, diluent, or adjuvant. For example, in any of the methods of the invention, the method comprises administering to a mammalian subject or patient a pharmaceutical composition comprising a therapeutically effective amount of dapagliflozin or dapagliflozin-PGS and at least one pharmaceutically acceptable carrier, diluent, or adjuvant.

In any of the methods of the invention, the method comprises administering to a mammalian subject or patient a pharmaceutical composition comprising a therapeutically effective amount of an SGLT2 inhibitor (i.e., for treating obesity, enhancing glucosuria, and/or effecting weight loss), wherein the amount of SGLT2 inhibitor is an amount below that prescribed in generally accepted medical practice for treating diabetes and at least one pharmaceutically acceptable carrier, diluent, or adjuvant. For example, in any of the methods of the invention, the method comprises administering to a mammalian subject or patient a pharmaceutical composition comprising a therapeutically effective amount of dapagliflozin or dapagliflozin-PGS (i.e., for treating obesity, enhancing glucosuria, and/or effecting weight loss) wherein the amount of dapagliflozin or dapagliflozin-PGS is an amount below that prescribed in generally accepted medical practice for treating diabetes and at least one pharmaceutically acceptable carrier, diluent, or adjuvant.

Still further in accordance with the invention, in any of the methods of the invention, the method comprises administering to a mammalian subject or patient a pharmaceutical composition comprising a therapeutically effective amount of an SGLT2 inhibitor in combination with one or more other anti-obesity agent(s) as defined herein and known in the art, and at least one pharmaceutically acceptable carrier, diluent, or adjuvant. For example, in any of the methods of the invention, a pharmaceutical composition comprising a therapeutically effective amount of dapagliflozin or dapagliflozin-PGS is administered in combination with one or more other anti-obesity agent(s) as defined herein and known in the art, and at least one pharmaceutically acceptable carrier, diluent, or adjuvant.

Also, in any of the methods of the invention, the method comprises administering to a mammalian subject or patient a pharmaceutical composition comprising a therapeutically effective amount of an SGLT2 inhibitor (i.e., for treating obesity, enhancing glucosuria, and/or effecting weight loss) and one or more other anti-obesity agent(s), wherein the amount of SGLT2 inhibitor is an amount below that prescribed in generally accepted medical practice for treating diabetes and at least one pharmaceutically acceptable carrier, diluent, or adjuvant. For example, in any of the methods of the invention, the method comprises administering to a mammalian subject or patient a pharmaceutical composition comprising a therapeutically effective amount of dapagliflozin or dapagliflozin-PGS (i.e., for treating obesity, enhancing glucosuria, and/or effecting weight loss) and one or more other anti-obesity agent(s), wherein the amount of dapagliflozin or dapagliflozin-PGS is an amount below that prescribed in generally accepted medical practice for treating diabetes and at least one pharmaceutically acceptable carrier, diluent, or adjuvant.

Also, in any of the methods of the invention, the method comprises administering to a mammalian subject or patient a pharmaceutical composition comprising a therapeutically effective amount of an SGLT2 inhibitor (i.e., for treating obesity, enhancing glucosuria, and/or effecting weight loss) and one or more other anti-diabetic agent(s), wherein the amount of SGLT2 inhibitor is an amount below that prescribed in generally accepted medical practice for treating diabetes and at least one pharmaceutically acceptable carrier, diluent, or adjuvant. For example, in any of the methods of the invention, the method comprises administering to a mammalian subject or patient a pharmaceutical composition comprising a therapeutically effective amount of dapagliflozin or dapagliflozin-PGS (i.e., for treating obesity, enhancing glucosuria, and/or effecting weight loss) and one or more other anti-diabetic agent(s), wherein the amount of dapagliflozin or dapagliflozin-PGS is an amount below that prescribed in generally accepted medical practice for treating diabetes and at least one pharmaceutically acceptable carrier, diluent, or adjuvant.

Thus, for example, methods are provided for treating obesity in a mammalian subject or patient, including a human subject or patient, comprising administering to a mammalian subject or patient in need of such treatment a pharmaceutical composition comprising a therapeutically effective amount of an SGLT2 inhibitor and at least one pharmaceutically acceptable carrier, diluent, or adjuvant. In one embodiment, a method for treating obesity in a mammalian subject or patient, including a human subject or patient, with type II diabetes mellitus is provided comprising administering to the subject or patient a pharmaceutical composition comprising a therapeutically effective amount of an SGLT2 inhibitor and at least one pharmaceutically acceptable carrier, diluent, or adjuvant. In other embodiments, methods for treating obesity in a mammalian subject or patient, including a human subject or patient, with or without type II diabetes mellitus comprise administering to the subject or patient a pharmaceutical composition comprising a therapeutically effective amount of an SGLT2 inhibitor in combination with one or more other anti-obesity agent(s) as defined herein and known in the art, and at least one pharmaceutically acceptable carrier, diluent, or adjuvant. In another embodiment, a method for treating obesity in a mammalian subject or patient, including a human subject or patient, with or without type II diabetes comprises administering to the subject or patient a pharmaceutical composition comprising a therapeutically effective amount of an SGLT2 inhibitor (i.e., for treating obesity), wherein the amount of SGLT2 inhibitor is an amount below that prescribed in generally accepted medical practice for treating diabetes and at least one pharmaceutically acceptable carrier, diluent, or adjuvant. In another embodiment, a method for treating obesity in a mammalian subject or patient, including a human subject or patient, with or without type II diabetes comprises administering to the subject or patient a pharmaceutical composition comprising a therapeutically effective amount of an SGLT2 inhibitor (i.e., for treating obesity) and one or more other anti-obesity agent(s), wherein the amount of SGLT2 inhibitor is an amount below that prescribed in generally accepted medical practice for treating diabetes and at least one pharmaceutically acceptable carrier, diluent, or adjuvant. In one embodiment of any of the above-described methods and pharmaceutical compositions, the SGLT2 inhibitor is dapagliflozin or dapagliflozin-PGS.

In addition, methods are provided for promoting, increasing or enhancing glucosuria in a mammalian subject or patient, including a human subject or patient, to effect weight loss comprising administering to a mammalian subject or patient a pharmaceutical composition comprising a therapeutically effective amount of an SGLT2 inhibitor and at least one pharmaceutically acceptable carrier, diluent, or adjuvant. In one embodiment, a method for promoting, increasing or enhancing glucosuria in a mammalian subject or patient, including a human subject or patient, with type II diabetes mellitus to effect weight loss is provided comprising administering to the subject or patient a pharmaceutical composition comprising a therapeutically effective amount of an SGLT2 inhibitor and at least one pharmaceutically acceptable carrier, diluent, or adjuvant. In other embodiments, methods for promoting, increasing or enhancing glucosuria in a mammalian subject or patient, including a human subject or patient, with or without type II diabetes mellitus to effect weight loss comprise administering to the subject or patient a pharmaceutical composition comprising a therapeutically effective amount of an SGLT2 inhibitor in combination with one or more other anti-obesity agent(s) as defined herein and known in the art and at least one pharmaceutically acceptable carrier, diluent, or adjuvant. In another embodiment, a method for promoting, increasing or enhancing glucosuria in a mammalian subject or patient, including a human subject or patient, with or without type II diabetes to effect weight loss comprises administering to the subject or patient a pharmaceutical composition comprising a therapeutically effective amount of an SGLT2 inhibitor (i.e., for enhancing glucosuria), wherein the amount of SGLT2 inhibitor is an amount below that prescribed in generally accepted medical practice for treating diabetes and at least one pharmaceutically acceptable carrier, diluent, or adjuvant. In another embodiment, a method for promoting, increasing or enhancing glucosuria in a mammalian subject or patient, including a human subject or patient, with or without type II diabetes to effect weight loss comprises administering to the subject or patient a pharmaceutical composition comprising a therapeutically effective amount of an SGLT2 inhibitor (i.e., for enhancing glucosuria) and one or more other anti-obesity agent(s), wherein the amount of SGLT2 inhibitor is an amount below that prescribed in generally accepted medical practice for treating diabetes and at least one pharmaceutically acceptable carrier, diluent, or adjuvant. In one embodiment of any of the above-described methods and pharmaceutical compositions, the SGLT2 inhibitor is dapagliflozin or dapagliflozin-PGS.

In addition, methods are provided for causing weight loss in a mammalian subject or patient, including a human subject or patient, who may or may not be characterized as obese, comprising administering to a mammalian subject or patient a pharmaceutical composition comprising a therapeutically effective amount of an SGLT2 inhibitor and at least one pharmaceutically acceptable carrier, diluent, or adjuvant. In one embodiment, a method for causing weight loss in a mammalian subject or patient, including a human subject or patient, with type II diabetes mellitus who may or may not be characterized as obese, is provided comprising administering to the subject or patient a pharmaceutical composition comprising a therapeutically effective amount of an SGLT2 inhibitor and at least one pharmaceutically acceptable carrier, diluent, or adjuvant. In other embodiments, methods for causing weight loss in a mammalian subject or patient, including a human subject or patient, with or without type II diabetes mellitus who may or may not be characterized as obese comprise administering to the subject or patient a pharmaceutical composition comprising a therapeutically effective amount of an SGLT2 inhibitor in combination with one or more other anti-obesity agent(s) as defined herein and known in the art and at least one pharmaceutically acceptable carrier, diluent, or adjuvant. In another embodiment, a method for causing weight loss in a mammalian subject or patient, including a human subject or patient, with or without type II diabetes who may or may not be characterized as obese, comprises administering to the subject or patient a pharmaceutical composition comprising a therapeutically effective amount of an SGLT2 inhibitor (i.e., for causing weight loss), wherein the amount of SGLT2 inhibitor is an amount below that prescribed in generally accepted medical practice for treating diabetes and at least one pharmaceutically acceptable carrier, diluent, or adjuvant. In another embodiment, a method for causing weight loss in a mammalian subject or patient, including a human subject or patient, with or without type II diabetes who may or may not be characterized as obese, comprises administering to the subject or patient a pharmaceutical composition comprising a therapeutically effective amount of an SGLT2 inhibitor (i.e., for causing weight loss) and one or more other anti-obesity agent(s), wherein the amount of SGLT2 inhibitor is an amount below that prescribed in generally accepted medical practice for treating diabetes and at least one pharmaceutically acceptable carrier, diluent, or adjuvant. In one embodiment of any of the above-described methods and pharmaceutical compositions, the SGLT2 inhibitor is dapagliflozin or dapagliflozin-PGS.

The invention further provides pharmaceutical compositions comprising compounds of the invention formulated together with one or more non-toxic pharmaceutically acceptable carriers, diluents, or adjuvants and the like. In one embodiment, the invention provides a pharmaceutical composition comprising a therapeutically effective amount of an SGLT2 inhibitor and at least one pharmaceutical acceptable carrier, diluent, or adjuvant. In another embodiment, the invention provides a pharmaceutical composition comprising a therapeutically effective amount of an SGLT2 inhibitor (i.e., for treating obesity, enhancing glucosuria, and/or causing weight loss), wherein the amount of the SGLT2 inhibitor is an amount below that prescribed in generally accepted medical practice for treating diabetes, and at least one pharmaceutical acceptable carrier, diluent, or adjuvant.

In one embodiment, the invention provides a pharmaceutical composition comprising a therapeutically effective amount of an SGLT2 inhibitor and one or more other anti-obesity agent(s) or other anti-diabetic agent(s) and at least one pharmaceutically acceptable carrier, diluent, or adjuvant. In another embodiment, the invention provides a pharmaceutical composition comprising a therapeutically effective amount of an SGLT2 inhibitor (i.e., for treating obesity, enhancing glucosuria, and/or causing weight loss) and one or more other anti-obesity agent(s) or other anti-diabetic agent(s), wherein the amount of SGLT2 inhibitor is an amount below that prescribed in generally accepted medical practice for treating diabetes and at least one pharmaceutically acceptable carrier, diluent, or adjuvant. In any of the above-described embodiments of pharmaceutical compositions, the SGLT2 inhibitor can be dapagliflozin or dapagliflozin-PGS.

As discussed, in certain embodiments of the inventive methods provided herein, the SGLT2 inhibitor is administered in combination with one or more anti-obesity agents, which anti-obesity agents can be another SGLT2 inhibitor as described herein and/or can be an anti-obesity agent other than an SGLT2 inhibitor. Examples of suitable anti-obesity agents that are not SGLT2 inhibitors include, but are not limited to, β-3 adrenergic agonists; lipase inhibitors; serotonin (and dopamine) reuptake inhibitors; thyroid beta compounds; anorectic agents; Neuropeptide Y (NPY) antagonists; leptin analogs; MC4 agonists; and other anti-obesity agents, as well as other anti-diabetic agents. In one embodiment of any of the inventive methods, the anti-obesity agent(s) is administered in a therapeutically effective amount. In another embodiment of any of the inventive methods, the anti-obesity agent(s) is administered in an amount below the therapeutic amount as prescribed in generally accepted medical practice for treating diabetes.

In any of the inventive methods, the SGLT2 inhibitor can be administered in combination with one or more other anti-diabetic agents, which can be another SGLT2 inhibitor as described herein and/or can be an anti-diabetic agent other than an SGLT2 inhibitor. In one embodiment, the anti-diabetic agent(s) is administered in a therapeutically effective amount. In another embodiment, the anti-diabetic agent(s) is administered in an amount below that prescribed in generally accepted medical practice for treating diabetes.

In one embodiment of the inventive methods employing a combination of SGLT2 inhibitor(s) and anti-obesity agent(s) and/or anti-diabetic agent(s), the dosage for the other anti-obesity agent(s) and/or anti-diabetic agent(s) (used in combination with the SGLT2 inhibitor) is from about 20% of the lowest dose normally recommended for treating diabetes up to about 100% of the normally recommended dosage for treating diabetes. In another embodiment, the dosage for the other anti-obesity agent(s) and/or anti-diabetic agent(s) is from about 35% to about 90% of the normally recommended dosage for treating diabetes In one embodiment of the inventive methods employing a combination of SGLT2 inhibitor and anti-obesity and/or anti-diabetic agent(s), the SGLT2 inhibitor is administered in a weight ratio to the other anti-obesity agent(s) and/or anti-diabetic agent(s) in an amount within the range of from about 200:1 to about 0.1:1. In another embodiment, the SGLT2 inhibitor is administered in a weight ratio to the other anti-obesity agent(s) and/or anti-diabetic agent(s) in an amount within the range of from about 100:1 to about 0.2:1. In one embodiment, the SGLT2 inhibitor is administered in an amount below the amount that would induce hypoglycemia in mammals or patients that do not suffer from hypoglycemia prior to administration of the inhibitor.

The invention provides the use of an SLGT2 inhibitor in the manufacture of a medicament for the treatment of obesity. In one embodiment, the invention provides the use of a C-arylglucoside or O-arylglucoside in the manufacture of a medicament for the treatment of obesity. For example, the invention provides the use of Dapagliflozin or Dapagliflozin-PGS in the manufacture of a medicament for the treatment of obesity. The invention also provides the use of an SLGT2 inhibitor in the manufacture of a medicament to effect weight loss. In one embodiment, the invention provides the use of a C-arylglucoside or O-arylglucoside in the manufacture of a medicament to effect weight loss. For example, the invention provides the use of Dapagliflozin or Dapagliflozin-PGS in the manufacture of a medicament to effect weight loss. The invention further provides the use of an SLGT2 inhibitor in the manufacture of a medicament to enhance glucosuria. In one embodiment, the invention provides the use of a C-arylglucoside or O-arylglucoside in the manufacture of a medicament to enhance glucosuria. For example, the invention provides the use of Dapagliflozin or Dapagliflozin-PGS in the manufacture of a medicament to enhance glucosuria. In any of the described uses, the SLGT2 inhibitor is administered in a therapeutically effective amount. In any of the described uses, the SLGT2 inhibitor is administered in an amount below that prescribed in generally accepted medical practice for treating diabetes.

The invention provides an SLGT2 inhibitor for use in therapy in treating obesity. In one embodiment, the invention provides the use of a C-arylglucoside or O-arylglucoside for use in therapy in treating obesity. For example, the invention provides Dapagliflozin or Dapagliflozin-PGS for use in therapy in treating obesity. The invention also provides an SLGT2 inhibitor for use in therapy in effecting weight loss. In one embodiment, the invention provides the use of a C-arylglucoside or O-arylglucoside for use in therapy in effecting weight loss. For example, the invention provides Dapagliflozin or Dapagliflozin-PGS for use in therapy in effecting weight loss. The invention further provides an SLGT2 inhibitor for use in therapy in enhancing glucosuria. In one embodiment, the invention provides the use of a C-arylglucoside or O-arylglucoside for use in therapy in enhancing glucosuria. For example, the invention provides Dapagliflozin or Dapagliflozin-PGS for use in therapy in enhancing glucosuria. In any of the described uses, the SLGT2 inhibitor is administered in a therapeutically effective amount. In any of the described uses, the SLGT2 inhibitor is administered in an amount below that prescribed in generally accepted medical practice for treating diabetes.

The invention provides the combination of an SLGT2 inhibitor and one or more anti-obesity agent(s) as a medicament for treating obesity, enhancing glucosuria, or effecting weight loss. In one embodiment, the invention provides the combination of a C-arylglucoside or O-arylglucoside and one or more anti-obesity agent(s) as a medicament for treating obesity, enhancing glucosuria, or effecting weight loss. For example, the invention provides the combination of Dapagliflozin or Dapagliflozin-PGS and one or more anti-obesity agent(s) as a medicament for treating obesity, enhancing glucosuria, or effecting weight loss. The invention provides the combination of an SLGT2 inhibitor and one or more anti-diabetic agent(s) as a medicament for treating obesity, enhancing glucosuria, or effecting weight loss. In one embodiment, the invention provides the combination of a C-arylglucoside or O-arylglucoside and one or more anti-diabetic agent(s) as a medicament for treating obesity, enhancing glucosuria, or effecting weight loss. For example, the invention provides the combination of Dapagliflozin or Dapagliflozin-PGS and one or more anti-diabetic agent(s) as a medicament for treating obesity, enhancing glucosuria, or effecting weight loss. In any of the described uses, the SLGT2 inhibitor is administered in a therapeutically effective amount. In any of the described uses, the SLGT2 inhibitor is administered in an amount below that prescribed in generally accepted medical practice for treating diabetes.

In one specific embodiment, the invention provides the combination of Dapagliflozin-PGS and one or more beta 3 adrenergic agonists as a medicament for treating obesity, enhancing glucosuria, or effecting weight loss. In one specific embodiment, the invention provides the combination of Dapagliflozin-PGS and one or more lipase inhibitors as a medicament for treating obesity, enhancing glucosuria, or effecting weight loss. In one specific embodiment, the invention provides the combination of Dapagliflozin-PGS and one or more serotonin (and dopamine) reuptake inhibitors as a medicament for treating obesity, enhancing glucosuria, or effecting weight loss. In one specific embodiment, the invention provides the combination of Dapagliflozin-PGS and one or more thyroid receptor beta drugs as a medicament for treating obesity, enhancing glucosuria, or effecting weight loss. In one specific embodiment, the invention provides the combination of Dapagliflozin-PGS and one or more MCH-1 receptor antagonists as a medicament for treating obesity, enhancing glucosuria, or effecting weight loss. In one specific embodiment, the invention provides the combination of Dapagliflozin-PGS and one or more agonists of the 5-HT2c receptor as a medicament for treating obesity, enhancing glucosuria, or effecting weight loss. In one specific embodiment, the invention provides the combination of Dapagliflozin-PGS and one or more anorectic agents as a medicament for treating obesity, enhancing glucosuria, or effecting weight loss. In one specific embodiment, the invention provides the combination of Dapagliflozin-PGS and one or more Neuropeptide Y (NPY) antagonists as a medicament for treating obesity, enhancing glucosuria, or effecting weight loss. In one specific embodiment, the invention provides the combination of Dapagliflozin-PGS and one or more Leptin analogs as a medicament for treating obesity, enhancing glucosuria, or effecting weight loss. In one specific embodiment, the invention provides the combination of Dapagliflozin-PGS and one or more MC4 receptor agonists as a medicament for treating obesity, enhancing glucosuria, or effecting weight loss. In one specific embodiment, the invention provides the combination of Dapagliflozin-PGS and one or more antagonists of the cannabinoid receptor as a medicament for treating obesity, enhancing glucosuria, or effecting weight loss. In any of the described uses, the Dapagliflozin-PGS is administered in a therapeutically effective amount. In any of the described uses, the Dapagliflozin-PGS is administered in an amount below that prescribed in generally accepted medical practice for treating diabetes.

The invention provides the use of an SLGT2 inhibitor in the manufacture of a medicament for the treatment of obesity, enhancing glucosuria, or effecting weight loss in which such treatment comprises a combination with one or more anti-obesity agent(s), for concurrent or sequential use, in any order. In one embodiment, the invention provides the use of a C-arylglucoside or O-arylglucoside in the manufacture of a medicament for the treatment of obesity, enhancing glucosuria, or effecting weight loss in which such treatment comprises a combination with one or more anti-obesity agent(s), for concurrent or sequential use, in any order. For example, the invention provides the use of Dapagliflozin or Dapagliflozin-PGS in the manufacture of a medicament for the treatment of obesity, enhancing glucosuria, or effecting weight loss in which such treatment comprises a combination with one or more anti-obesity agent(s), for concurrent or sequential use, in any order. In any of the described uses, the SLGT2 inhibitor is administered in a therapeutically effective amount. In any of the described uses, the SLGT2 inhibitor is administered in an amount below that prescribed in generally accepted medical practice for treating diabetes.

In one specific embodiment, the invention provides the use of Dapagliflozin-PGS in the manufacture of a medicament for the treatment of obesity, enhancing glucosuria, or effecting weight loss in which such treatment comprises a combination with one or more beta 3 adrenergic agonists, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more lipase inhibitors, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more serotonin (and dopamine) reuptake inhibitors, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more thyroid receptor beta drugs, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more MCH-1 receptor antagonists, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more agonists of the 5-HT2c receptor, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more Neuropeptide Y (NPY) antagonists, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more Leptin analogs, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more MC4 receptor agonists, for concurrent or sequential use, in any order. In one specific embodiment, the invention provides the use of Dapagliflozin-PGS in the manufacture of a medicament for the treatment of obesity, enhancing glucosuria, or effecting weight loss in which such treatment comprises a combination with one or more antagonists of the cannabinoid receptor, for concurrent or sequential use, in any order. In any of the described uses, the Dapagliflozin-PGS is administered in a therapeutically effective amount. In any of the described uses, the Dapagliflozin-PGS is administered in an amount below that prescribed in generally accepted medical practice for treating diabetes.

DETAILED DESCRIPTION OF THE INVENTION

Figure 1:
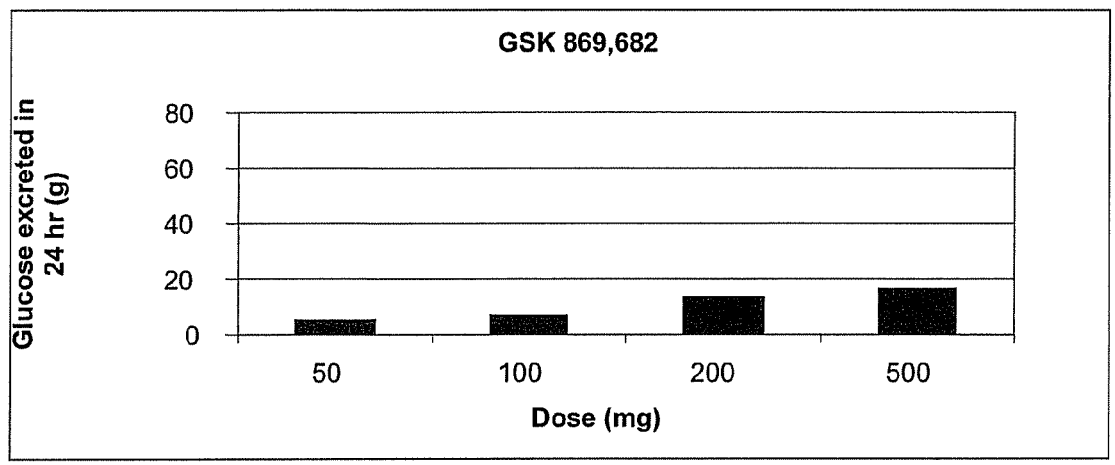
FIG. 1 depicts two bar graphs showing an indirect comparison of the amount of glucose excretion in urine/day caused by each of the SGLT2 inhibitors GSK 869,682 (top graph) and Dapagliflozin-PGS (bottom graph).
Figure 1:
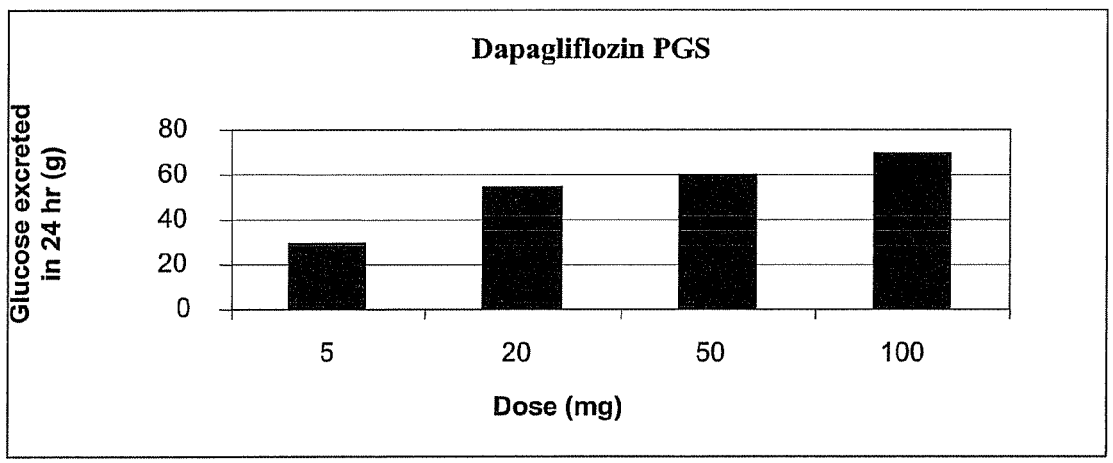

The term "obesity" as employed herein refers to a body weight 20% or more over that set out in standard (normal) height-weight tables, (such as disclosed in The Merck Manual), or a body mass index (BMI) greater or equal to 28. The present invention provides methods and compositions for causing weight reduction in subjects or patients who suffer from obesity and thus, according to generally accepted medical practice, should lose 20% or more of body weight, or subjects or patients who are not technically obese as defined herein, but need or would like to lose anywhere from about 1% to about 20% of body weight.

The term "glucosuria" as used herein refers to excretion of glucose in the urine.

The term "SGLT2 inhibitor in an amount below that prescribed in generally accepted medical practice for treating diabetes" or "SGLT2 inhibitor in an amount below the effective amount for treating diabetes" refers to an amount or dose of SGLT2 inhibitor which does not cause a significant reduction in blood glucose levels in a mammalian subject or patient and does not cause hypoglycemia in a mammalian subject or patient.

The term "therapeutically effective amount of an SLGT2 inhibitor" as used herein refers to an amount or dose of SLGT2 inhibitor that effects weight loss and/or enhances glucosuria in a mammalian subject or patient.

The term "Dapagliflozin-PGS" as used herein refers to Dapagliflozin propylene glycol solvate or Dapagliflozin propylene glycol hydrate, including the (S) form and the (R) form of Dapagliflozin propylene glycol.

The term "hypoglycemia" as employed herein refers to a blood glucose level of below 60 mg per deciliter (dL).

The term "diabetes" as employed herein refers to type 2 (or Type II) diabetes or non-insulin dependent diabetes mellitus (NIDDM) wherein a patient has inadequate glycemic control ($HbA_{1C}$<7%) with diet and exercise.

The term "pharmaceutically acceptable carrier" as used herein means a non-toxic, inert solid, semi-solid or liquid filler, diluent, encapsulating material or formulation auxiliary of any type. Some examples of materials which can serve as pharmaceutically acceptable carriers are sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such a propylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions, as well as other non-toxic compatible lubricants, such as sodium lauryl sulfate and magnesium stearate; coloring agents; releasing agents; coating agents; sweetening; flavoring; and perfuming agents; preservatives; and antioxidants.

The invention provides pharmaceutical compositions comprising compounds of the invention formulated together with one or more non-toxic pharmaceutically acceptable carriers, diluents, or adjuvants. The pharmaceutical compositions can be formulated for oral administration in solid or liquid form, for parenteral injection or for rectal administration. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters, such as ethyl oleate. Proper fluidity can be maintained, for example, by the use of a coating such as lecithin, by the maintenance of the required particle size in the case of dispersions, and by the use of surfactants.

These compositions can also contain adjuvants, such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It can also be desirable to include isotonic agents, for example, sugars, sodium chloride and the like. Prolonged absorption of the injectable pharmaceutical form can be brought about by the use of agents delaying absorption, for example, aluminum monostearate and gelatin.

In carrying out the methods of the invention for treating mammalian subjects or patients, the SGLT2 inhibitor can be administered to a mammalian subject or patient in need of treatment in a weight-reducing amount which can be as high as an amount used to treat diabetes (elevated blood glucose levels) but less than an amount which causes hypoglycemia. The daily dose is adjusted depending upon the mammalian subject or patient and the specific SGLT2 inhibitor employed. The dose can be lowered as successful weight loss is achieved. In one embodiment, the SGLT2 inhibitor is administered to a mammalian subject or patient in a weight-reducing amount which is an amount used to treat diabetes (elevated blood glucose levels) and less than an amount which causes hypoglycemia. For example, in one embodiment, the SGLT2 inhibitor is orally administered in an amount of from about 1 mg to about 1000 mg per day. In another embodiment, the SGLT2 inhibitor is orally administered in an amount of from about 1 mg to about 100 mg/day. In another embodiment, the SGLT2 inhibitor is orally administered in an amount of from about 2.5 mg to about 75 mg/day. In another embodiment, the SGLT2 inhibitor is orally administered in an amount of from about 20 mg to about 50 mg/day. All of the described dosages can be administered in a single dose or in the form of individual doses from 1 to 4 times per day, for example.

In one embodiment, the SGLT2 inhibitor is administered to a mammalian subject or patient in need of treatment in a weight-reducing amount which is below the amount required to treat diabetes and less than an amount which causes hypoglycemia. For example, in one embodiment, the SGLT2 inhibitor is orally administered in an amount of from about 2 mg to about 75 mg/day. In another embodiment, the SGLT2 inhibitor is orally administered in an amount of from about 2.5 to about 50 mg/day. The described dosages can be administered in a single dose or in the form of individual doses from 1 to 4 times daily, for example.

In one embodiment, the methods of the invention comprise administrating the SGLT2 inhibitor dapagliflozin propylene glycol hydrate (referred to as Dapagliflozin-PGS or Dapa-PGS), as disclosed in U.S. application Ser. No. 11/765,481, published as US 2008-0004336 A1, which is herein incorporated by reference in its entirety for any purpose. The Dapa-PGS can be in the (S) form or the (R) form. The (S) form of Dapa-PGS is shown below as Compound I.

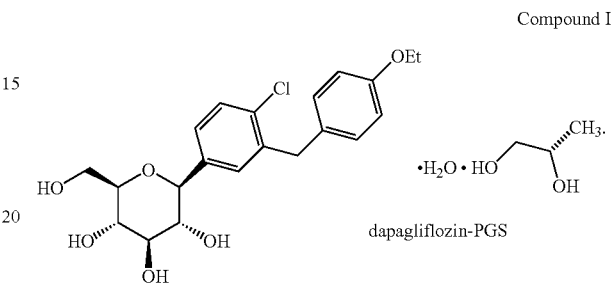

Compound I dapagliflozin-PGS

The (R) form of Dapa-PGS is shown below as Compound IA.

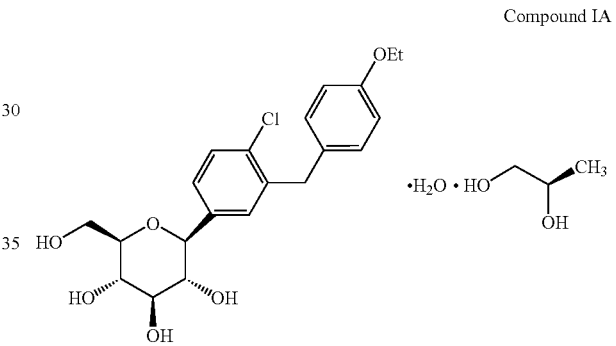

Compound IA

Figure 5:
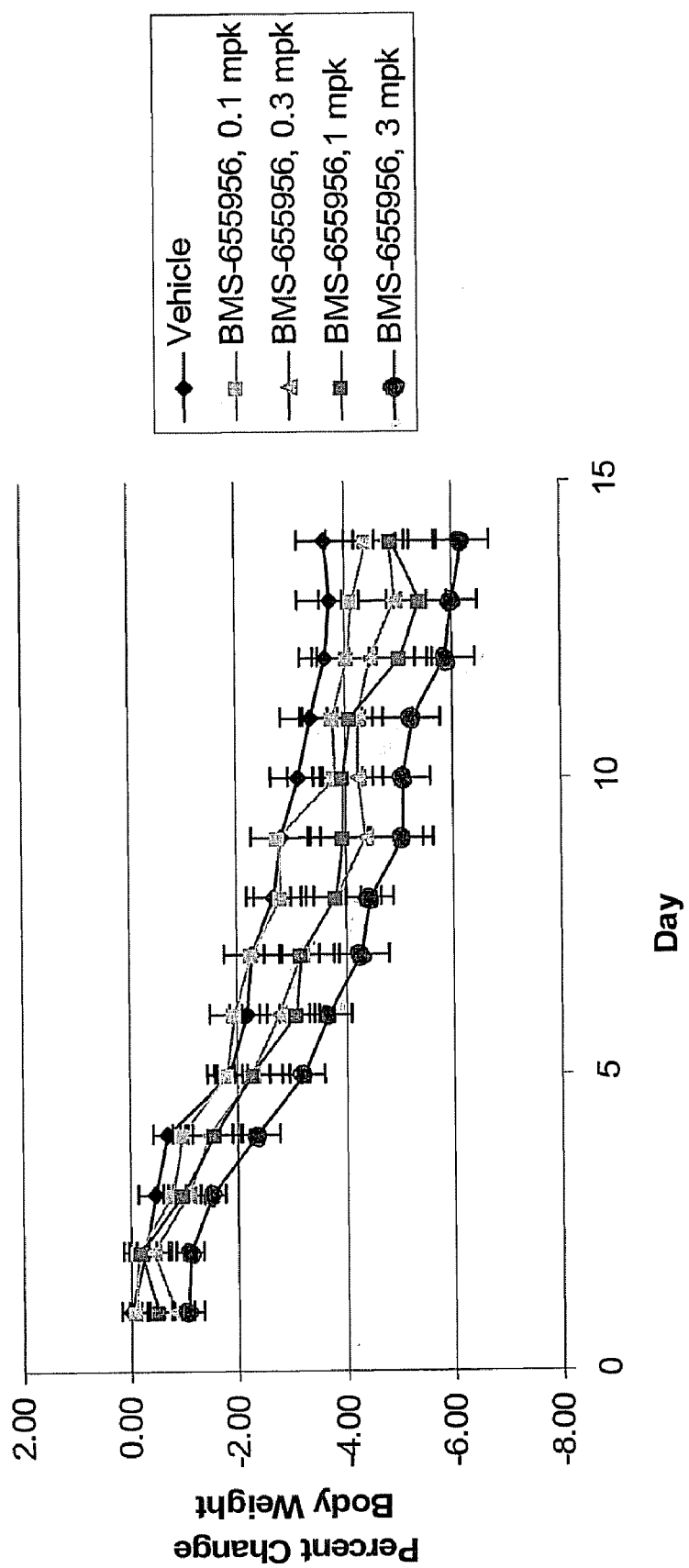
FIG. 5 depicts weight loss in diet-induced obese rats treated with BMS-655956 (Compound IIIA).

The crystalline structure of dapa-PGS is characterized by one or more of the following:

a) unit cell parameters substantially equal to the following:
Cell dimensions:
a=11.2688(8)Å
b=4.8093(3)Å
c=46.723(3)Å
α=90 degrees
β=90 degrees
γ=90 degrees
Space group=$P2_12_12_1$,
Molecules/asymmetric unit=1
wherein measurement of said crystalline structure is at room temperature and which is characterized by fractional atomic coordinates substantially as listed in Table 4 of U.S. Provisional Application No. 60/817,118 and in U.S. non-provisional application Ser. No. 11/765,481 (US 2008-0004336 A1);

b) a powder x-ray diffraction pattern comprising 2θ values (CuKαλ=1.5418 Å) selected from the group consisting of 3.8±0.1, 7.6±0.1, 8.1±0.1, 8.7±0.1, 15.2±0.1, 15.7.4±0.1, 17.1±0.1, 18.9±0.1 and 20.1±0.1, at room temperature;

c) a solid state $^{13}C$ NMR spectrum having substantially similar peak positions at 16.2, 17.6, 39.3, 60.9, 63.3, 69.8, 76.9, 78.7, 79.4, 113.8, 123.6, 129.3, 130.5, 132.0, 135.7, 139.1 and 158.0 ppm, as determined on a 400 MHz spectrometer relative to TMS at zero;

d) a differential scanning calorimetry thermogram having an endotherm in the range of about 50° C. to 78° C. or as shown in FIG. 7 of U.S. Provisional Application No. 60/817,118 and in U.S. non-provisional application Ser. No. 11/765,481 (US 2008-0004336 A1);

e) thermal gravimetric analysis curve with about 18.7% weight loss from about room temperature up to about 240° C. or as shown in FIG. 5 of U.S. Provisional Application No. 60/817,118 and in U.S. non-provisional application Ser. No. 11/765,481 (US 2008-0004336 A1); or f) having a proton NMR having substantially similar peak positions as listed in Table 1A of U.S. Provisional Application No. 60/817,118 and in U.S. non-provisional application Ser. No. 11/765,481 (US 2008-0004336 A1).

SGLT2 inhibitors suitable for use in accordance with the present invention also include C-arylglucosides and O-arylglucosides.

Examples of C-arylglucoside (also referred to as C-glucosides) SGLT2 inhibitors useful in the methods of the invention, include, but are not limited to, the following.

1) C-arylglucosides as described in U.S. Pat. No. 6,515,117 and PCT/US03/15591, the disclosures of which are incorporated herein by reference in their entireties for any purpose. In one embodiment, the C-arylglucoside is dapagliflozin or (2S,3R,4R,5S,6R)-2-(4-chloro-3-(4-ethoxybenzyl)phenyl)-6-(hydroxymethyl)tetrahydro-2H-pyran-3,4,5-triol, shown below as Compound II.

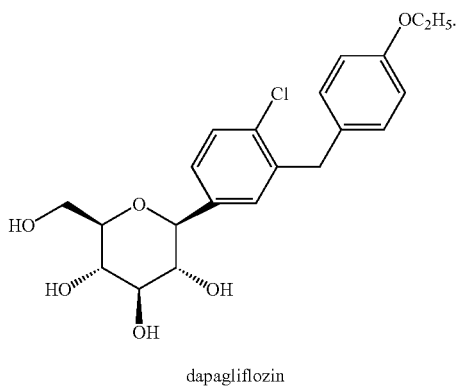

dapagliflozin

In another embodiment, the C-arylglucoside is the tetraacetate analog of dapagliflozin or (2R,3R,4R,5S,6S)-2-(acetoxymethyl)-6-(4-chloro-3-(4-ethoxybenzyl)phenyl)tetrahydro-2H-pyran-3,4,5-triyl triacetate, also disclosed in U.S. Pat. No. 6,515,117 and PCT/US03/15591, and shown below as Compound IIA.

Compound IIA

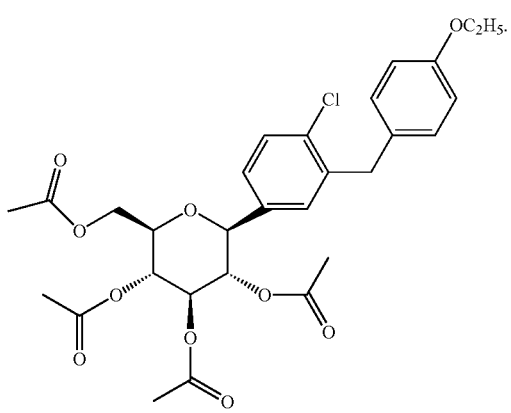

2) The C-arylglucosides, or pharmaceutically acceptable salts thereof, as described in U.S. Pat. No. 6,414,126 and PCT/US00/27187, the disclosures of which are incorporated herein by reference in their entireties for any purpose, including compounds of Formula III

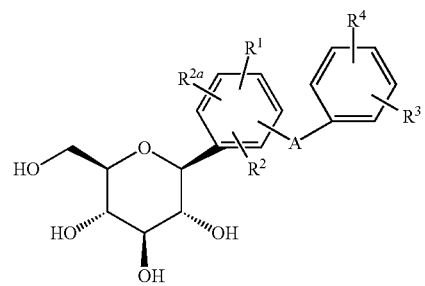

wherein $R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which can contain 1 to 4 heteroatoms in the ring which are N, O, S, SO, and/or $SO_2$;

$R^3$ and $R^4$ are independently hydrogen, OH, $OR^{5a}$, OAryl, $OCH_2$Aryl, alkyl, cycloalkyl, $CF_3$, —$OCHF_2$, —$OCF_3$, halogen, —CN, —$CO_2R^{5b}$, —$CO_2H$, $COR^{6b}$, —$CH(OH)R^{6c}$, —$CH(OR^{5h})R^{6d}$, —$CONR^6R^{6a}$, —$NHCOR^{5c}$, —$NHSO_2R^{5d}$, —$NHSO_2$Aryl, Aryl, —$SR^{5e}$, —$SOR^{5f}$, —$SO_2R^{5g}$—$SO_2$Aryl, or a five, six or seven membered heterocycle which can contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which can contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which can contain 1 to 4 heteroatoms in the ring which are N, O, S, SO, and/or $SO_2$; and A is O, S, NH, or $(CH_2)_n$ where n is 0-3, and a pharmaceutically acceptable salt thereof, all stereoisomers thereof, and all prodrug esters thereof, provided that when A is $(CH_2)_n$ where n is 0, 1, 2, or 3 or A is O, and at least one of $R^1$, $R^2$, and $R^{2a}$ is OH or $OR^5$, then at least one of $R^1$, $R^2$, and $R^{2a}$ is $CF_3$, $OCF_3$, or $OCHF_2$ and/or at least one of $R^3$ and $R^4$ is $CF_3$, —$OCHF_2$, —$OCF_3$, $CH(OR^{5h})R^{6d}$, $CH(OH)R^{6c}$, $COR^{6b}$, —CN, —$CO_2R^{5b}$, —$NHCOR^{5c}$, $NHSO_2R^{5d}$, —$NHSO_2$Aryl, Aryl, $SR^{5e}$, —$SOR^{5f}$, —$SO_2R^{5g}$ or —$SO_2$Aryl.

In another embodiment, the compound is (2S,3R,4R,5S,6R)-2-(4-chloro-3-(4-ethylbenzyl)phenyl)-6-(hydroxymethyl)tetrahydro-2H-pyran-3,4,5-triol disclosed in U.S. patent application Ser. No. 11/233,617 and US 2006/0063722 A1 and shown below as Compound IIIA Compound IIIA

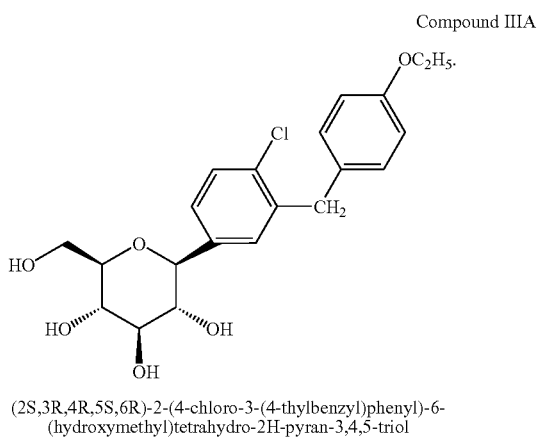

(2S,3R,4R,5S,6R)-2-(4-chloro-3-(4-thylbenzyl)phenyl)-6-(hydroxymethyl)tetrahydro-2H-pyran-3,4,5-triol 3) C-aryl glucosides that are crystalline complexes of a D- or L-amino acid as described in PCT/US02/11066, US 2003/0064935, and U.S. Pat. No. 6,774,112, the disclosures of which are incorporated herein by reference for any purpose in their entireties. The C-aryl glucosides comprise crystalline D- or L-amino acid complexes of Formula IV

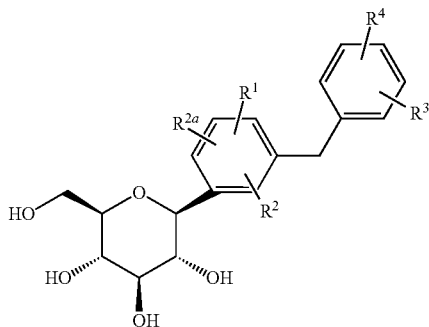

wherein
$R^1$, $R^2$ and $R^{2a}$ are independently hydrogen, OH, $OR^5$, alkyl, —$OCHF_2$, —$OCF_3$, —$SR^{5a}$ or halogen;
$R^3$ and $R^4$ are independently hydrogen, OH, $OR^{5b}$, alkyl, cycloalkyl, $CF_3$, —$OCHF_2$, —$OCF_3$, halogen, —$CONR^6R^{6a}$, —$CO_2R5c$, —$CO_2H$, —$COR^{6b}$, —CH(OH)$R^{6c}$, —CH($OR^{5d}$)$R^{6d}$, —CN, —$NHCOR^{5e}$, —$NHSO_2R^{5f}$, —$NHSO_2Aryl$, —$SR^{5g}$, —$SOR^{5h}$, —$SO_2R^{5f}$, or a five, six or seven membered heterocycle which can contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which can contain 1 to 4 heteroatoms in the ring which are N, O, S, SO, $SO_2$;
$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;
$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which can contain 1 to 4 heteroatoms in the ring which are N, O, S, SO, and/or $SO_2$, which are disclosed as being useful for treating obesity.

In one embodiment, the crystalline amino acid complexes include the L-proline, L-phenylalanine, and D-phenylalanine complexes where $R^{2a}$, $R^2$, and $R^4$ are hydrogen, $R^1$ is 4-Cl, and $R^3$ is 4-$C_2H_5$ or 4-$OC_2H_5$.

4) The glucopyranosyl-substituted benzene derivatives of formula V or pharmaceutically acceptable salts thereof, as described in US 2005/0209166, the disclosure of which is incorporated by reference in its entirety for any purpose, formula V

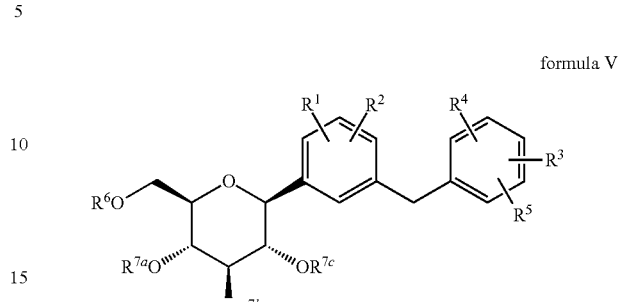

wherein $R^1$, $R^2$, $R^3$, $R^4$, $R^5$, $R^6$, $R^{7a}$, $R^{7b}$ and $R^{7c}$ are as defined in US 2005/0209166.

5) D-pyranosyl-substituted phenyl compounds of formula VI or pharmaceutically acceptable salts thereof, as described in US 2006/0074031, the disclosure of which is incorporated herein by reference in its entirety for any purpose, formula VI

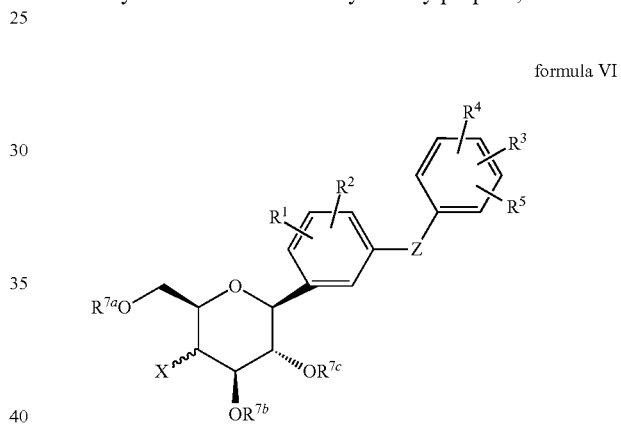

wherein $R^1$, $R^2$, $R^3$, $R^4$, $R^5$, $R^{7a}$, $R^{7b}$, $R^{7c}$, X and Z are as defined in US 2006/0074031.

6) D-xylopyranosyl-substituted compounds of formula VII or pharmaceutically acceptable salts thereof, as described in US 2006/0035841, the disclosure of which is incorporated herein by reference for any purpose, formula VII

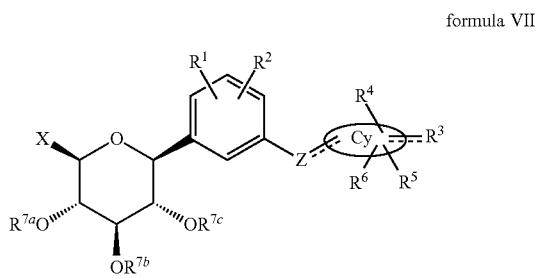

wherein ═══ denotes a single or double bond, and Cy, $R^1$, $R^2$, $R^3$, $R^4$, $R^5$, $R^6$, $R^{7a}$, $R^{7b}$, $R^{7c}$, X and Z are as defined in US 2006/0035841.

7) D-xylopyranosyl-substituted phenyl compounds of formula VIII or pharmaceutically acceptable salts thereof, as described in US 2006/0009400, the disclosure of which is incorporated herein by reference in its entirety for any purpose, formula VIII

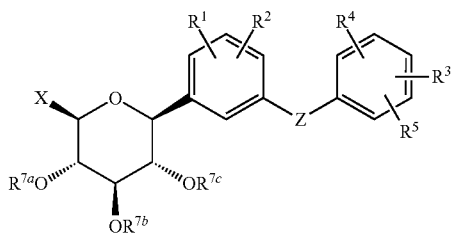

wherein $R^1$, $R^2$, $R^3$, $R^4$, $R^5$, $R^{7a}$, $R^{7b}$, $R^{7c}$, X and Z are as disclosed in US 2006/0009400.

8) D-glucopyranosyl-phenyl-substituted compounds of formula IX or pharmaceutically acceptable salts thereof, as described in US 2006/0025349, the disclosure of which is incorporated herein by reference in its entirety for any purpose, formula IX

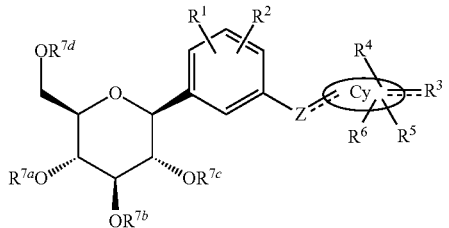

wherein - - - denotes a single or double bond, and Cy, $R^1$, $R^2$, $R^3$, $R^4$, $R^5$, $R^6$, $R^{7a}$, $R^{7b}$, $R^{7c}$, $R^{7d}$ and Z are as defined in US 2006/0025349.

9) C-glycoside derivatives of formula X or pharmaceutically acceptable salts thereof, as described in US 2006/0122126, the disclosure of which is incorporated herein by reference in its entirety for any purpose, formula X

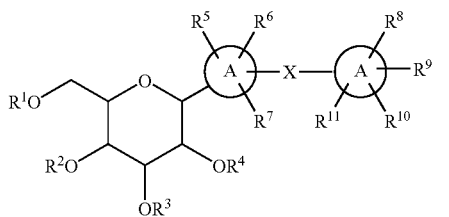

wherein $R^1$, $R^2$, $R^3$, $R^4$, $R^5$, $R^6$, $R^7$, $R^8$, $R^9$, $R^{10}$, $R^{11}$, X, A and B are as defined in US 2006/0122126.

10) D-xylopyranosyl-substituted phenyl compounds of formula XI or pharmaceutically acceptable salts thereof as described in US 2006/0019948, the disclosure of which is incorporated herein by reference in its entirety for any purpose, formula XI

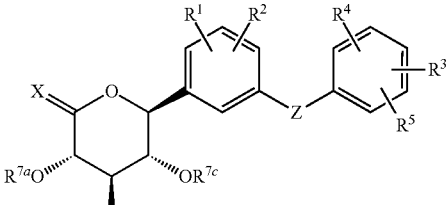

wherein $R^1$, $R^2$, $R^3$, $R^4$, $R^5$, $R^6$, $R^{7a}$, $R^{7b}$, $R^{7c}$, X and Z are as defined in US 2006/0019948.

Examples of O-glucoside SGLT2 inhibitors useful in the methods of the invention include, but are not limited to, the following:

1) 5-Thio-β-D-glucopyranoside compounds of formula XII or pharmaceutically acceptable salts or hydrates thereof, as described in US 2006/0194809, the disclosure of which is incorporated by reference in its entirety for any purpose, formula XII

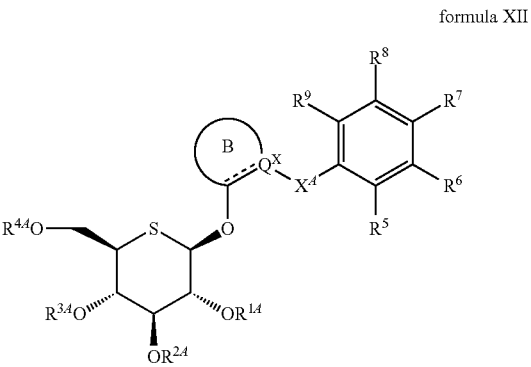

wherein $R^{1A}$, $R^{2A}$, $R^{3A}$, $R^{4A}$, $R^5$, $R^6$, $R^7$, $R^8$, $R^9$, $Q^x$, $X^A$ and B are as defined in US 2006/0194809.

2) Glucopyranyloxybenzene derivatives of formula XIII as described in WO 03/01180, the disclosure of which is incorporated by reference in its entirety, for any purpose, formula XIII

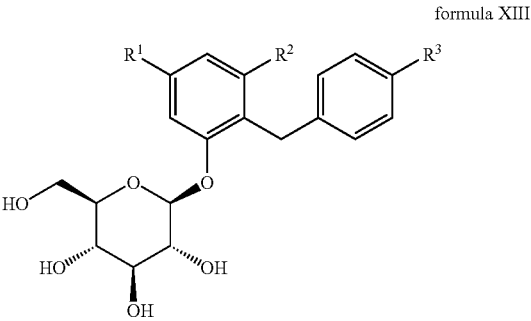

wherein
$R^1$ represents hydrogen, hydroxyl, optionally substituted amino, cyano, carbamoyl, optionally substituted lower alkyl, optionally substituted lower alkoxy, or optionally substituted cyclic amino;
$R^2$ represents hydrogen or lower alkyl; and
$R^3$ represents optionally substituted aryl, optionally substituted cycloalkyl, an optionally substituted aliphatic heterocyclic group, or an optionally substituted aromatic heterocyclic group, a pharmacologically acceptable salt of the derivative, or a prodrug of either.

3) Pyrazole derivatives of formula XIV or XV or pharmaceutically acceptable salts thereof, as described in U.S. Pat.

No. 6,908,905, the disclosure of which is incorporated herein by reference in its entirety for any purpose,

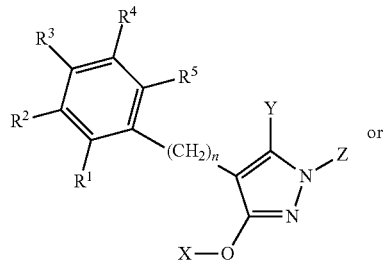
formula XIV

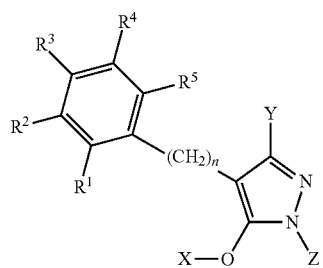
formula XV wherein

X represents β-D-glucopyranosyl group, wherein one or more hydroxyl groups can be acylated;

Y represents a lower alkyl group or a perfluoro lower alkyl group;

Z represents a cyclic alkyl group which can have a substituent(s), a cyclic unsaturated alkyl group which can have a substituent(s), a lower alkyl group having a cyclic alkyl group which can have a substituent(s), or a lower alkyl group having a cyclic unsaturated alkyl group which can have a substituent(s);

$R^1$ to $R^5$ can be the same or different and each represent a hydrogen atom, a lower alkyl group, a perfluoro lower alkyl group, a lower alkyloxy group, a perfluoro lower alkoxyl group, a lower alkylthio group, a perfluoro lower alkylthio group, a lower alkylamino group, a halogen group, a lower alkanoyl group, an alkenyl group, a cyclic alkenyl group, an alkynyl group, a phenyl group which can have a substituent(s), or a lower alkoxycarbonyl group; and n is an integer of 0 to 3 including

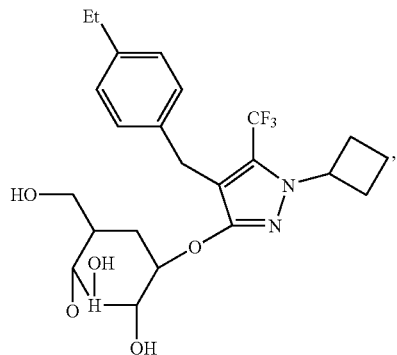

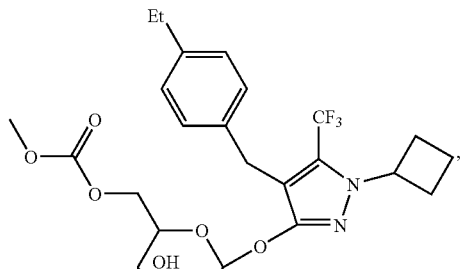

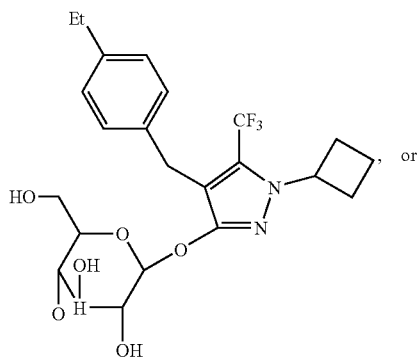
, or

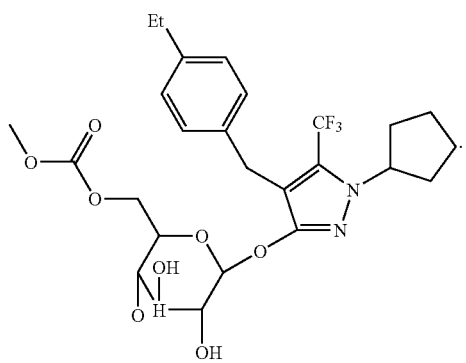

4) Pyrazole compounds of formula XVI or XVII or pharmaceutically acceptable salts thereof, as described in U.S. Pat. No. 6,815,428, the disclosure of which is incorporated herein by reference in its entirety for any purpose, formula XVI

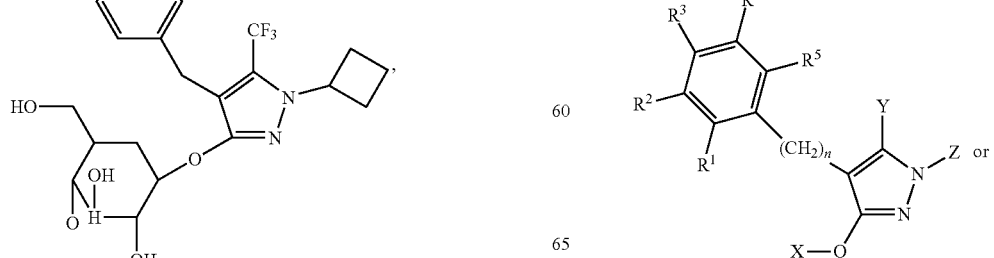

formula XVII

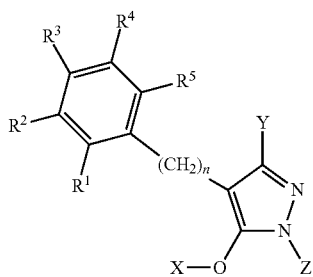

wherein

X represents a β-D-glucopyranosyl group, of which one or more hydroxyl groups can be acylated or a β-D-glucuronyl group, of which one or more hydroxyl groups can be acylated and a carboxyl group can be esterified;

Y represents a lower alkyl group or a perfluoro lower alkyl group;

Z represents a hydrogen atom, a lower alkyl group, a perfluoro lower alkyl group, an aralkyl group or a phenyl group;

$R^1$, $R^2$, $R^4$ and $R^5$ can be the same or different and each represents a hydrogen atom, a lower alkyl group, a perfluoro group, a lower alkoxy group, a fluoro lower alkoxy group, a lower alkylthio group, a perfluoro lower alkylthio group, a lower alkyl amino group, a halogen group, a lower alkanoyl group, a lower alkenyl group or a lower alkynyl group; and n represents an integer from 0 to 3, wherein at least one of $R^1$, $R^2$, $R^4$ and $R^5$ represents a lower alkyl group having 1 to 6 carbon atoms, lower alkylthio group having 1 to 6 carbon atoms, halogen atom, lower alkoxy group lower alkenyl group or lower alkynyl group; and $R^3$ represents a lower alkyl group having a 1 to 6 carbon atoms, a lower alkylthio group having 1 to 6 carbon atoms, a halogen atom, a lower alkoxy group, a lower alkenyl group, or a lower alkynyl group.

5) O-glucosylated benzamide compounds of formula XVIII or pharmaceutically acceptable salts thereof as described in U.S. Pat. No. 6,555,519, the disclosure of which is incorporated herein by reference in its entirety for any purpose, formula XVIII

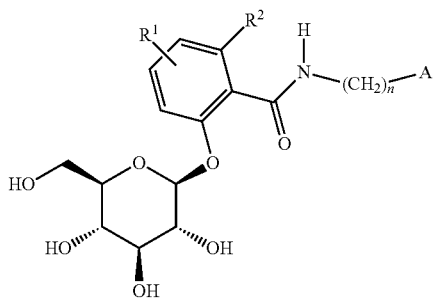

wherein n is 0, 1 or 2;

A is

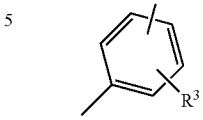

or heteroaryl which can contain 1 to 4 heteroatoms in the ring which can be selected from N, O, S, SO, and/or $SO_2$ bearing substituents $R^3$ and $R^4$;

$R^1$ is selected from hydrogen, $OR^5$, lower alkyl, aryl, arylalkyl, $NHCOR^5$, $NR^6R^{6a}$, or halogen;

$R^2$ is selected from hydrogen, OH, $OR^{5a}$, or lower alkyl;

$R^3$ an $R^4$ are the same or different and are independently selected from hydrogen, OH, $OR^{5b}$, OAryl, $OCH_2$Aryl, lower alkyl, cycloalkyl, aryl, arylalkyl, $CF_3$, $—SCF_3$, $—OCHF_2$, $—OCF_3$, halogen, $—CN$, $—CO_2R^{5c}$, $—CO_2H$, $—CONR^{6b}$, $R^{6c}$, $—NR^{6d}R^{6e}$, $—SO_2NH_2$, $—NHCOR^{5d}$, $—NHSO_2R^{5e}—NHSO_2$Aryl, $—SR^{5f}$, $—SOR^{5g}$, $—SO_2R^{5h}$, $—SO_2$ Aryl, $—OCH_2CO_2R^{5i}$, $—OCH_2CO_2H$, $—OCH_2CONR^{6f}R^{6g}$, $—OCH_2CH_2NR^{6h}R^{6i}$, or a five, six or seven membered heterocycle which can contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which can contain 1 to 4 heteroatom in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$, and $R^{5i}$ are independently lower alkyl;

$R^6$, $R^{6a}$, $R^{6b}$, $R^{6c}$, $R^{6d}$, $R^{6e}$, $R^{6f}$, $R^{6g}$, $R^{6h}$, and $R^{6i}$ are the same or different and are independently selected from hydrogen, alkyl, aryl, arylalkyl or cycloalkyl.

6) O-arylglucoside compounds of formula XIX or pharmaceutically acceptable salts thereof as described in U.S. Pat. No. 6,683,056, the disclosure of which is incorporated herein by reference in its entirety for any purpose, formula XIX

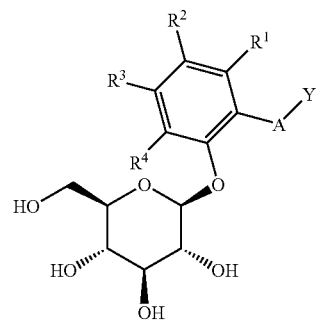

wherein when Y is

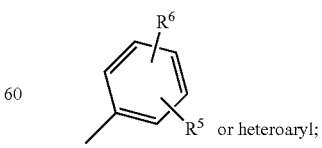

or heteroaryl;

$R^1$, $R^2$, $R^3$, and $R^4$ are the same or different and are independently selected from hydrogen, OH, $OR^7$, lower alkyl, or halogen, or two of $R^1$, $R^2$, $R^3$, and $R^4$ together with the carbons to which they are attached can form an annelated five, six or seven membered carbocycle or heterocycle which can contain 1 to 4 heteroatoms in the ring which are N, O, S, SO, and/or $SO_2$;

$R^5$ and $R^6$ are the same or different and are independently selected from hydrogen, OH, $OR^{7a}$, —OAryl, —$OCH_2$Aryl, lower alkyl, cycloalkyl, Aryl, arylalkyl, $CF_3$, arylalkenyl, —$OCHF_2$, —$OCF_3$, halogen, —CN, —$CO_2R^{7b}$, —$CO_2H$, $COR^{8f}$, $CHOHR^{8g}$, $CH(OR^{7h})R^{8h}$, —$CONR^8R^{8a}$, —$NHCOR^{7c}$, —$NHSO_2R^{7d}$, —$NHSO_2$Aryl, —$SR^{7e}$, —$SOR^{7f}$, —$SO_2R^{7g}$, —$SO_2$Aryl, —$OCH_2CO_2R^{7i}$, —$OCH_2CO_2H$, —$OCH_2CONR^{8b}R^{8c}$, —$OCH_2CH_2NR^{8d}R^{8e}$, or a five, six or seven membered heterocycle which can contain 1 to 4 heteroatoms in the ring which are N, O, S, SO, and/or $SO_2$, or $R^5$ and $R^6$ together with the carbons to which they are attached form an annelated five, six or seven membered carbocycle or heterocycle which can contain 1 to 4 heteroatoms in the ring which are N, O, S, SO, and/or $SO_2$;

$R^7$, $R^{7a}$, $R^{7b}$, $R^{7c}$, $R^{7d}$, $R^{7e}$, $R^{7f}$, $R^{7g}$, $R^{7h}$, and $R^{7i}$ are independently lower alkyl;

$R^8$, $R^{8a}$, $R^{8b}$, $R^{8c}$, $R^{8d}$, $R^{8e}$, $R^{8f}$, $R^{8g}$, and $R^{8h}$ are the same or different and are independently selected from hydrogen, alkyl, aryl, arylalkyl, cycloalkyl, or together with the nitrogen to which they are attached form an annelated five, six or seven membered heterocycle which can contain 1 to 4 heteroatoms in the ring which are N, O, S, SO, and/or $SO_2$;

A is $O(CH_2)_m$, S, $NH(CH_2)_m$, or $(CH_2)_n$ where n is 0-3 and m is 0-2.

Other O-aryl glucosides SGLT2 inhibitors which can be used in the present invention are described in the following references, all of which are incorporated herein by reference in their entireties for any purpose.

1) EP 598359A1 (JP 035988 and U.S. Pat. No. 5,731,292), the disclosures of which are incorporated herein by reference for any purpose, discloses compounds of formula XX, as shown formula XX

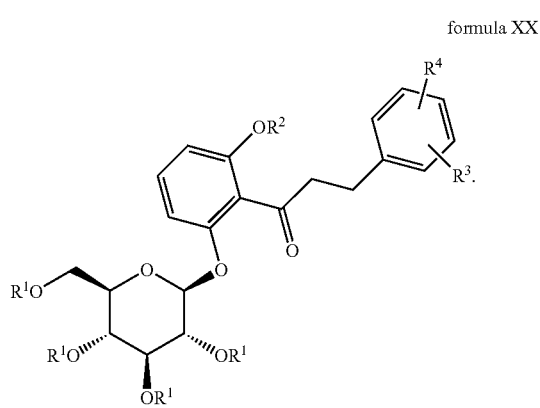

$R^1$ = H, acyl,
$R^2$ = H, Me
$R^3$ and $R^4$ as defined in EP 598359 A1

2) EP 0850948A1 (U.S. Pat. No. 6,048,842), the disclosure of which is incorporated herein by reference in its entirety for any purpose, discloses compounds of formula XXI, as shown formula XXI

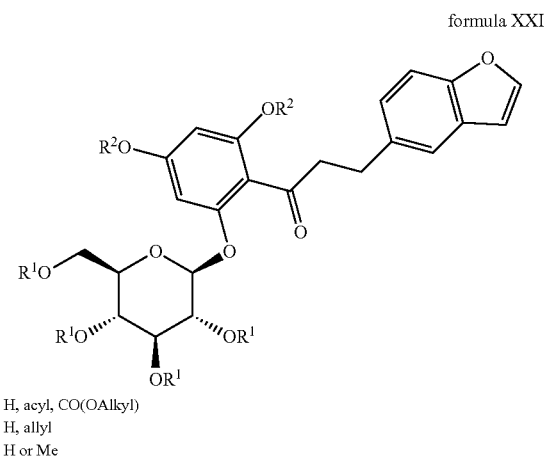

$R^1$ = H, acyl, CO(OAlkyl)
$R^2$ = H, allyl
$R^3$ = H or Me

3) JP 09188625A, the disclosure of which is herein incorporated by reference for any purpose in its entirety, discloses compounds of formula XXII as shown, where $R^3$ is H, ----- represents a single or double bond, and X=S or $CH_2$.

formula XXII

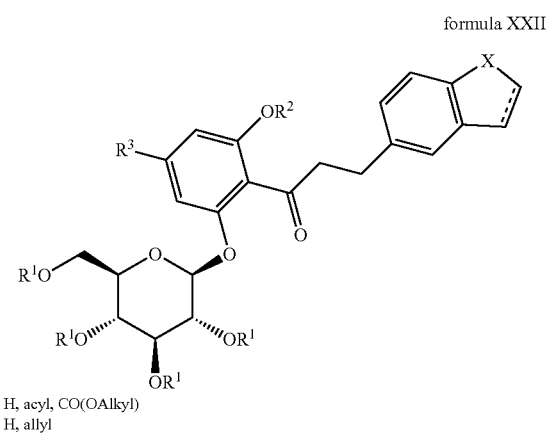

$R^1$ = H, acyl, CO(OAlkyl)
$R^2$ = H, allyl
$R^3$ = H

4) JP 09124685A, the disclosure of which is herein incorporated by reference in its entirety for any purpose, includes derivatives of formula XXIII as shown, where aryl group of C(O)-aryl or C(O)O-aryl is a substituted benzoic or pyridyl carboxylic acid or a urethane generated from the corresponding phenol.

formula XXIII

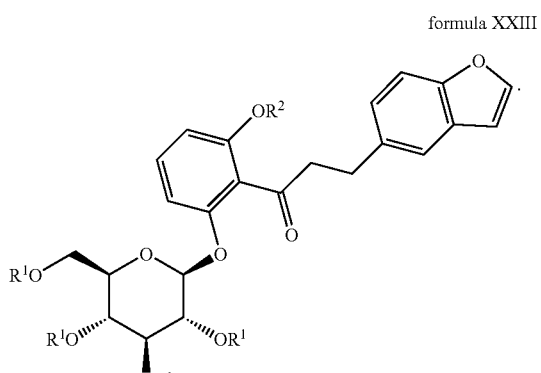

$R^1$ = H, acyl, C(O)aryl, C(O)Oaryl
$R^2$ = H

5) JP 09124684, the disclosure of which is herein incorporated by reference for any purpose in its entirety, discloses derivatives of formula XXIV, as shown

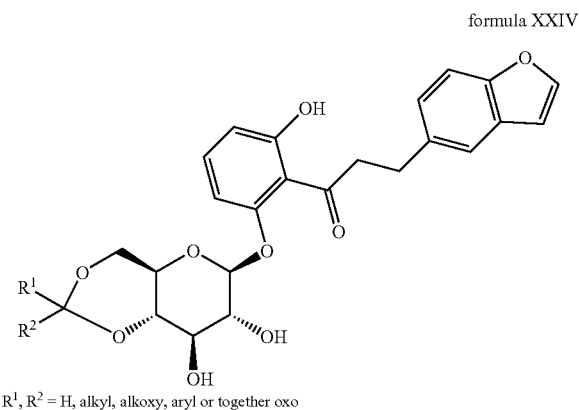

formula XXIV $R^1, R^2$ = H, alkyl, alkoxy, aryl or together oxo

6) EP 773226-A1 (U.S. Pat. No. 5,767,094), the disclosure of which is herein incorporated by reference in its entirety for any purpose, discloses derivatives of formula XXV, as shown.

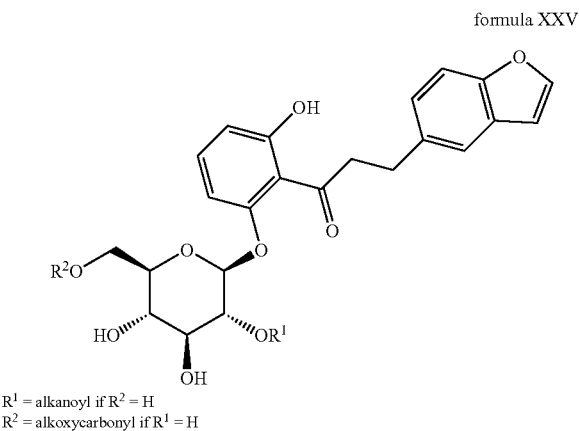

formula XXV $R^1$ = alkanoyl if $R^2$ = H
$R^2$ = alkoxycarbonyl if $R^1$ = H

7) JP 08027006-A, the disclosure of which is herein incorporated by reference in its entirety for any purpose, discloses derivatives of formula XXV as shown where various combinations of the glucose hydroxyl are acylated, similar to those disclosed in EP 598359A1.
8) EP 684254-A1, the disclosure of which is herein incorporated by reference in its entirety for any purpose, discloses compounds of formula XXII (shown above) similar to those described in JP 09188625A.

Other disclosures and publications which disclose SGLT2 inhibitors that can be employed in the methods of the invention are as follows:
9) K. Tsujihara et al., *Chem. Pharm. Bull.*, 44:1174-1180 (1996);
10) M. Hongu et al., *Chem. Pharm. Bull.*, 46:22-33 (1998);
11) M. Hongu et al., *Chem. Pharm. Bull.*, 46:1545-1555 (1998); and
12) A. Oku et al., *Diabetes*, 48:1794-1800 (1999).
13) JP 10245391 (Dainippon) discloses 500 structures as hypoglycemic agents for treatment of diabetes. These are O-glucosides of hydroxylated coumarins.

In addition to the above SGLT2 inhibitors, other SGLT2 inhibitors that can be employed in the methods of the invention include those disclosed in US 2005/0233982 (Boehringer Ingelheim Corp.), US 2005/0119192 (Kissei Pharmaceutical Co.), WO 2006/035796 (Kissei Pharmaceutical Co.), JP 2006/117651 (Taisho Pharmaceutical Co.), JP 2004/4359630 (Yamanouchi Pharmaceutical Co.), WO 2006/080421 (Chugai Seiyaku Kabushiki Kaishi), US 2005/0233988 (Tanabe Seiyaku Co.), WO 2005/012321 (Tanabe Seiyaku Co.), U.S. Pat. No. 7,015,201 (Ajinomoto Co.), WO 2006/058597 (Merck Patent GmbH), WO 2006/011469 (Chugai Seiyaku Kabushiki Kaisha), US 2003/0195235 (Johnson & Johnson), and WO 2006/037537 (Boehringer Ingelheim), the disclosures of which are herein incorporated by reference in their entireties for any purpose.

Other types of anti-obesity agents that can be optionally employed with the SGLT2 inhibitor include one or more of the following: beta 3 adrenergic agonist(s), lipase inhibitor(s), serotonin (and dopamine) reuptake inhibitor(s), thyroid receptor beta drug(s), MCH-1 receptor antagonist(s), agonist(s) of the 5-HT2c receptor, anorectic agent(s), Neuropeptide Y (NPY) antagonist(s), such as an NPY5 antagonist and an NPY2 antagonist, Leptin analog(s), MC4 receptor agonist(s), and/or antagonist(s) of the cannabinoid receptor.

Examples of suitable beta 3 adrenergic agonists that can be optionally administered in combination with the SGLT2 inhibitor include, but are not limited to, AJ9677 (Takeda/Dainippon), SB-418790, L750355 (Merck), CP331648 (Pfizer), and other known beta 3 agonists as disclosed in U.S. Pat. Nos. 5,541,204, 5,770,615, 5,491,134, 5,776,983 and 5,488,064. In one embodiment, the beta 3 adrenergic agonist is selected from the group consisting of AJ9677, L750355, and CP331648.

Examples of suitable lipase inhibitors that can be optionally administered in combination with the SGLT2 inhibitor include, but are not limited to, orlistat and ATL-962 (Alizyme). In one embodiment, the lipase inhibitor is orlistat.

Examples of suitable serotonin (and dopamine) reuptake inhibitors that can be optionally administered in combination with the SGLT2 inhibitor include, but are not limited to, sibutramine, topiramate (Johnson & Johnson), axokine (Regeneron), dexphenfluramine, and tetrahydrolipostatin. In one embodiment, the serotonin (and dopamine) reuptake inhibitor is selected from the group consisting of sibutramine and topiramate.

Examples of suitable thyroid receptor beta compounds that can be optionally administered in combination with the SGLT2 inhibitor include, but are not limited to, thyroid receptor ligands as disclosed in WO 97/21993 (U. Cal SF), WO 99/00353 (KaroBio) and WO 00/039077 (GB98/284425) (KaroBio). In one embodiment, the thyroid receptor beta compound is selected from the compounds disclosed in WO 99/00353 and WO 00/039077.

Examples of suitable anorectic agents that can be optionally administered in combination with the SGLT2 inhibitor include, but are not limited to, dexamphetamine, phentermine, phenylpropanolamine and mazindol. In one embodiment, the anorectic agent is dexamphetamine.

The various anti-obesity agents described above can be employed in the same dosage form with the SGLT2 inhibitor or in different dosage forms, in dosages and regimens as generally known in the art or in the Physician's Desk Reference.

In carrying out the method of the invention, a pharmaceutical composition is employed comprising an SGLT2 inhibitor and optionally another anti-obesity agent, in association with a pharmaceutical carrier, vehicle or diluent. The pharmaceutical composition can be formulated employing conventional solid or liquid vehicles, diluents, and pharmaceutical additives as appropriate for the mode of desired administration. The compounds can be administered to mammalian species, including humans, monkeys, dogs, and other mammals by a variety of routes including, for example, orally, in the form of tablets, capsules, granules, powders, and the like, parenterally, in the form of injectable preparations, intranasally, rectally, and transdermally, in the form of patches, for example.

The amount of drug required for therapeutic effect varies with the agent chosen, the nature and severity of the condition, and the mammal undergoing treatment, and is ultimately at the discretion of the physician. Furthermore, the optimal quantity and spacing of individual dosages of a drug is determined by the nature and extent of the weight loss desired, the form, route, and site of administration, the particular mammal or patient being treated. In one embodiment, the SGLT2 inhibitor dose for adults is between 1 and 350 mg per day, which can be administered in a single dose or in the form of individual doses from 1-4 times per day. The dose administered is adjusted according to the age, weight, and condition of the mammal or patient, as well as the route of administration, dosage form and regimen, and the desired result. Such dosages and forms of administration is determined using conventional techniques. It is also appreciated that the optimal course of treatment, that is, the number of doses given, can be ascertained by those skilled in the art using conventional course of treatment determination tests.

The above dosage forms can also include the necessary physiologically acceptable carrier material, excipient, lubricant, buffer, antibacterial, bulking agent (such as mannitol), and the like.

The various formulations of the invention can optionally include one or more fillers or excipients in an amount within the range of from about 0% to about 90% by weight and preferably from about 1% to about 80% by weight. Examples of suitable excipients include, but are not limited to, lactose, sugar, corn starch, modified corn starch, mannitol, sorbitol, inorganic salts, such as calcium carbonate, and cellulose derivatives, such as wood cellulose and microcrystalline cellulose.

One or more binders can be present in addition to or in lieu of the fillers in an amount within the range of from about 0% to about 35%. In one embodiment, the binders are present in an amount of from about 0.5% to about 30% by weight of the composition. Examples of suitable binders include polyvinylpyrrolidone (molecular weight ranging from about 5000 to about 80,000 and preferably about 40,000), lactose, starches, such as corn starch, modified corn starch, sugars, gum acacia and the like, as well as a wax binder in finely powdered form (less than 500 microns), such as carnauba wax, paraffin, spermaceti, polyethylenes and microcrystalline wax.

Where the composition is in the form of a tablet, it can include one or more tableting lubricants in an amount within the range of from about 0.2% to about 8% by weight of composition. In one embodiment, the lubricant(s) is in an amount within the range of from about 0.5% to about 2% by weight of the composition. Examples of suitable lubricants include, but are not limited to, magnesium stearate, stearic acid, palmitic acid, calcium stearate, talc, carnauba wax, and the like. Other ingredients can optionally be present, including, for example, preservatives, stabilizers, colorants, anti-adherents and silica flow conditioners or glidants, such as Syloid brand silicon dioxide.

Tablets of the invention can also optionally include a coating layer which can comprise from about 0% to about 15% by weight of the tablet composition. The coating layer can comprise any conventional coating formulations that can include, for example, one or more film-formers or binders and/or one or more plasticizers. Examples of suitable film-formers or binders include, but are not limited to, hydrophilic polymers, such as hydroxypropylmethylcellulose, hydrophobic polymers, such as methacrylic acid esters, neutral polymers, ethyl cellulose, cellulose acetate, polyvinyl alcohol-maleic anhydride copolymers, β-pinene polymers, glyceryl esters of wood resins and the like. Examples of suitable plasticizers include, but are not limited to, triethyl citrate, diethyl phthalate, propylene glycol, glycerin, butyl phthalate, castor oil and the like. Both core tablets as well as coating formulations can contain aluminum lakes to provide color.

The film formers are applied from a solvent system containing one or more solvents including water, alcohols such as methyl alcohol, ethyl alcohol and isopropyl alcohol, ketones such as acetone and ethylmethyl ketone, chlorinated hydrocarbons such as methylene chloride, dichloroethane, and 1,1,1-trichloroethane.

Where a color is employed, the color can be applied together with the film former, plasticizer, and solvent compositions.

Examples of formulations containing an SGLT2 inhibitor for use herein and a process for preparing such formulations are set out in U.S. application Ser. No. 60/896,286 filed Mar. 22, 2007, the disclosure of which is incorporated herein by reference in its entirety for any purpose.

Examples of certain specific embodiments of tablet and capsule formulations in accordance with the invention are set out below.

TABLE I

Tablet and Capsule Formulations

| Material | Possible Range % by weight of tablet or capsule fill | Preferred Range % by weight of tablet or capsule fill |
|---|---|---|
| Dapagliflozin or Dapagliflozin PGS | 0.1 to 70% | 0.1 to 30% |
| Bulking Agent/binder | 1 to 95% | 10 to 85% |
| Anhydrous Lactose | 0 to 95% | 20 to 75% |
| Microcrystalline cellulose | 0 to 95% | 20 to 75% |
| Pregelatinized starch | 0 to 95% | 10 to 75% |
| Disintegrant | 0 to 20% | 0.25 to 10% |
| Croscarmellose sodium | 0 to 20% | 2 to 10% |
| Crospovidone | 0 to 12% | 4 to 10% |
| Sodium Starch glycolate | 0 to 20% | 2 to 10% |
| Lubricant | 0.1 to 5% | 0.2 to 2% |
| Magnesium Stearate | 0.1 to 5% | 0.2 to 2% |
| Anti adherent/glidant | 0 to 10% | 1 to 10% |
| Talc, silicon dioxide | | more preferably 1 to 4% |
| Outer Protective Coating Layer | % by weight of tablet or capsule fill | % by weight of tablet or capsule fill |
| Coating polymer, and optional plasticizer(s), glidant(s), anti-tacking agent(s), and colorant(s) | 0.5 to 50% | 1 to 5% |

II. Granulation Composition (% w/w) for Tablets and Capsules

| Ingredient | Range % by weight | Preferred range % by weight | Preferred formulation % w/w |
|---|---|---|---|
| Dapagliflozin or Dapagliflozin PGS | 0.1-40 | 5-15 | 9.84 |
| Microcrystalline Cellulose | q.s. | q.s. | 63.91 |
| Lactose Anhydrous | 0-50 | 10-30 | 20 |
| Crospovidone XL-10 | 1-15 | 3-10 | 4 |
| Silicon Dioxide | 0-6 | 0.5-4 | 1.5 |
| Magnesium Stearate | 0.0-4.0 | 0.5-2.0 | 0.75 | q.s. refers to the quantity sufficient to make the granulation composition 100% w/w.

A film coating for capsules or tablets of Table II comprises, for example, polyvinyl alcohol (PVA), titanium dioxide, polyethylene glycol 3350, talc, and colorant.

Tablets or capsules of various strengths (0.1-50 mg) can be prepared using different weights of the stock granulations described herein.

The pharmaceutical formulation for use in the method of the invention in the form of a tablet can be obtained by a process comprising the steps of:
a) mixing the inactive ingredients with the SGLT2 inhibitor (for example, Dapagliflozin PGS);
b) formulating granules;
c) drying and/or screening the granules;
d) blending the granules; and
e) tabletting the blend obtained in (d) into tablets.

In one embodiment, step a) of the process employs impact blending or milling and/or sizing equipment. In one embodiment, the granules in step b) of the process are formulated by dry granulation, wet granulation, or direct compression. In one embodiment, the granules are formulated by dry granulation. In one embodiment, the granules in step d) of the process are blended with a tabletting aid or a lubricant and filler.

The pharmaceutical formulation in the form of a capsule can be obtained by a process comprising the steps of:
a) mixing the inactive ingredients with the medicament using a combination of blending and milling processes;
b) formulating granules;
c) drying and/or screening the granules; and
(d) loading the granules into capsules.

In one embodiment, step a) of the process employs impact milling or blending and/or sizing equipment. In one embodiment, the granules in step b) of the process are formulated by dry granulation, wet granulation, or direct compression. In one embodiment, the granules are formulated by dry granulation.

The activity of dapagliflozin can be determined using, for example, using the assay system described below or any appropriate assay system known in the art. The mRNA sequence for human SGLT2 (GenBank #M95549) is cloned by reverse-transcription and amplification from human kidney mRNA, using standard molecular biology techniques. The cDNA sequence is stably transfected into CHO cells, and clones are assayed for SGLT2 activity essentially as described in Ryan et al., "HK-2: an immortalized proximal tubule epithelial cell line from normal adult human kidney", Kidney International, 45:48-57 (1994). Evaluation of inhibition of SGLT2 activity in a clonally selected cell line is performed essentially as described in Ryan et al. (1994), with the following modifications. Cells are grown in 96-well plates for 2-4 days to 75,000 or 30,000 cells per well in F-12 nutrient mixture (Ham's F-12), 10% fetal bovine serum, 300 ug/ml Geneticin and penicillin-streptomycin. At confluence, the cells are washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells are then incubated with 10 µM [$^{14}$C] AMG, and 10 µM inhibitor (final DMSO=0.5%) in 10 mM Hepes/Tris, pH 7.4, 137 mM NaCl, 5.4 mM KCl, 2.8 mM $CaCl_2$, 1.2 mM $MgSO_4$ at 37° C. for 1.5 hours. Uptake assays are quenched with ice cold 1×PBS containing 0.5 mM phlorizin, and cells are then lysed with 0.1% NaOH. After addition of MicroScint scintillation fluid, the cells are allowed to shake for 1 hour, and then [$^{14}$C]AMG (glucose analog α-methyl-D-glucopyranoside) is quantitated on a TopCount scintillation counter. Controls are performed with and without NaCl. For determination of $EC_{50}$ values, 10 inhibitor concentrations (dapagliflozin) are used over 2 log intervals in the appropriate response range, and triplicate plates are averaged across plates.

While this invention has been particularly shown and described with references to preferred embodiments thereof, it will be understood by those skilled in the art that various changes in form and details may be made therein without departing from the scope of the invention encompassed by the appended claims. It will also be clear that the invention may be practiced otherwise than as particularly described in the foregoing description and examples. Numerous modifications and variations of the present invention are possible in light of the above teachings and, therefore, are within the scope of the appended claims.

The following examples are provided to describe the invention in further detail. These examples, which set forth the best mode presently contemplated for carrying out the invention, are intended to illustrate and not to limit the invention.

EXAMPLES

The following working Examples are illustrative of the present invention. All temperatures are expressed in degrees Centigrade unless otherwise indicated.

Capsules containing the SGLT2 inhibitor dapagliflozin or dapagliflozin PGS were prepared in strengths of 2.5 mg (Example 1), 10 mg (Example 2) and 100 mg (Example 3) (as the non-solvated form) as two-piece, gray opaque size #0 (2.5 mg and 10 mg) and size #00 (for 100 mg) capsule shell.

Example 1

Preparation of Dapagliflozin/Dapagliflozin-PGS Capsule, 2.5 mg

A 25.0 mg of stock granulation was prepared containing 10% dapagliflozin or dapagliflozin-PGS filled in gray, opaque, size #0 capsule shell.

A. Stock Granulation Composition

| Ingredient | Amount (% w/w) |
|---|---|
| Dapagliflozin (Or equivalent amount of Dapagliflozin propylene glycol hydrate) | 10.0 |
| Pregelatinized Starch | 15.0 |
| Microcrystalline Cellulose | 68.75 |
| Sodium Starch Glycolate | 3.0 |
| Silicon Dioxide | 2.0 |
| Magnesium Stearate | 1.25 |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The preferred amount of magnesium stearate is 1.25% (w/w). A useful range is 1.25-1.50% (w/w).

The stock granulation of Part A and the Example 1 capsules were prepared according to the following procedures.

B. Example 1 Stock Granulation Procedure
1. Screen dapagliflozin or dapagliflozin-PGS.
2. Screen silicon dioxide.
3. Mix silicon dioxide with dapagliflozin or dapagliflozin-PGS in a suitable blender.
4. Screen pregelatinized starch and microcrystalline cellulose, if necessary.
5. Add ingredients from Step 4 to a suitable blender.
6. Add mixture from Step 3 to the blend from Step 5, and mix.
7. Screen sodium starch glycolate.
8. Add ingredient from Step 7 to the blend from Step 6, and mix.
9. Screen the blend from Step 8, and mix.
10. Screen portion of magnesium stearate.
11. Add ingredient from Step 10 to the blend from Step 9, and mix.
12. Densify the blend from Step 11.
13. Reduce the densified blend Step 12.
14. Screen the remaining portion of magnesium stearate.
15. Add ingredient from Step 14 to the granulation from Step 13, and mix.

C. Example 1 Product: Dapagliflozin/Dapagliflozin-PGS Capsule, 2.5 mg
1. Fill empty capsule shells with sufficient Example 1 Part A stock granulation for capsules (10.0%) w/w (as the non-solvated form), to provide 2.5 mg capsules.
2. De-dust the capsules.

Example 2

Preparation of Dapagliflozin/Dapagliflozin-PGS Capsule, 10 mg

A. Stock Granulation Composition
Stock granulation composition was prepared as described in Example 1A.

B. Example 2 Stock Granulation Procedure
Stock granulation procedure was performed as described in Example 1B.

C. Example 2 Product: Dapagliflozin/Dapagliflozin-PGS Capsule, 10 mg
1. Fill empty capsule shells with Example 1 Part A stock granulation for capsules (10.0% w/was the non-solvated form), to provide 10 mg capsules.
2. De-dust the capsules.
3. Weight sort the capsules.

Example 3

Preparation of Dapagliflozin/Dapagliflozin-PGS Capsule, 100 mg

Composition: 438.6 mg of dapagliflozin (Example 3 Part A) Stock Granulation for Capsules (22.8% w/w), filled in Gray, Opaque, Size #0 Capsule Shell was prepared.

A. Stock Granulation Composition

| Ingredient | Amount (% w/w) |
|---|---|
| Dapagliflozin (Or equivalent amount of Dapagliflozin propylene glycol hydrate) | 22.8 |
| Pregelatinized Starch | 15.0 |
| Microcrystalline Cellulose | 55.95 |
| Sodium Starch Glycolate | 3.0 |
| Silicon Dioxide | 2.0 |
| Magnesium Stearate | 1.25 |

The amount of dapagliflozin is theoretically equivalent to 81.29% of dapagliflozin PG hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The preferred amount of magnesium stearate is 1.25% (w/w). A useful range is 1.25-1.50% (w/w).

The stock granulation of Part 3A and the Example 3 capsules were prepared according to the following procedures.

B. Stock Granulation Procedure
1. Screen silicon dioxide.
2. Mix silicon dioxide with dapagliflozin or dapagliflozin-PGS in a suitable blender.
3. Screen the blend from Step 2, and mix again.
4. Screen pregelatinized starch and microcrystalline cellulose, if necessary.
5. Add ingredients form Step 4 to the blend from Step 3, and mix.
6. Screen sodium starch glycolate.
7. Add ingredient from Step 6 to the blend from Step 5, and mix.
8. Screen a portion of magnesium stearate.
9. Add ingredient from Step 8 to the blend from Step 7, and mix.
10. Densify the blend from Step 9.
11. Reduce the densified blend from Step 10.
12. Screen the remaining portion of magnesium stearate.
13. Add ingredient from Step 12 to the granulation from Step 11, and mix.

C. Example 3 Product: Dapagliflozin/Dapagliflozin-PGS Capsule, 100 mg
1. Fill empty capsule shells with Example 3 stock granulation for capsules (22.8% w/w as the non-solvated form).
2. De-dust the capsules.
3. Weight sort the capsules.

The formed capsules of Example 1 (2.5 mg), Example 2 (10 mg), and Example 3 (100 mg) are used in treating metabolic disorders, including obesity.

Example 4

Preparation of Dapagliflozin/Dapagliflozin-PGS Tablet, 2.5 mg

Tablets containing the SGLT2 inhibitor of structure Ia (dapagliflozin) (S)-propylene glycol hydrate) were prepared in strengths of 2.5 mg (Example 4), 10 mg (Example 5) and 50 mg (Example 6) as described below.

Product: Dapagliflozin/Dapagliflozin-PGS Tablet, 2.5 mg

A. Tablet Composition

| Ingredient | Amount |
| --- | --- |
| Dapagliflozin propylene glycol hydrate (Or equivalent amount of Dapagliflozin) | 3.08 mg |
| Microcrystalline Cellulose | 67.11 mg |
| Anhydrous Lactose | 25.00 mg |
| Crospovidone | 8.75 mg |
| Croscarmellose Sodium | 3.75 mg |
| Talc | 12.50 mg |
| Silicon Dioxide | 2.88 mg |
| Magnesium Stearate | 1.94 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 1.94 mg. An acceptable range is about 1.55 to about 2.33 mg.

The stock granulation of Part 4A and the Example 4 tablets were prepared according to the following procedures.

B. Stock Granulation Procedure

1. Deaggregate dapagliflozin propylene glycol hydrate and magnesium stearate separately using a suitable screen.
2. Mix Dapagliflozin propylene glycol hydrate with a portion of microcrystalline cellulose in a suitable mixer; pass through a mill; and transfer it into a suitable blender.
3. "Dry Rinse" the mixer used for mixing Step 2 with a portion of microcrystalline cellulose.
4. Add the blend from Step 3 to the blend from Step 2.
5. Mix the mixture from Step 4 with remaining microcrystalline cellulose, portion of crospovidone, portion of croscarmellose sodium, portion of silicon dioxide and Anhydrous Lactose.
6. Add talc and intragranular magnesium stearate to the mixture from Step 5 and mix.
7. Compact the powder blend from Step 6.
8. Reduce compact from Step 7 to form granules.
9. Mix the granules from Step 8 with remaining amounts of crospovidone, croscarmellose sodium and silicon dioxide.
10. Mix the granules from Step 9 with remaining amount of magnesium stearate.

C. Example 4 Product: Dapagliflozin/Dapagliflozin-PGS Tablet, 2.5 mg

1. Setup the tabletting equipment.
2. Compress the Example 4 stock granulation into tablets.

Example 5

Preparation of Dapagliflozin/Dapagliflozin-PGS Tablet, 10 mg Product:
Dapagliflozin/Dapagliflozin-PGS Tablet, 10 mg A. Tablet Composition

| Ingredient | Amount |
| --- | --- |
| Dapagliflozin propylene glycol hydrate (Or equivalent amount of Dapagliflozin) | 12.30 mg |
| Microcrystalline Cellulose | 57.89 mg |
| Anhydrous Lactose | 25.00 mg |
| Crospovidone | 8.75 mg |
| Croscarmellose Sodium | 3.75 mg |
| Talc | 12.50 mg |
| Silicon Dioxide | 2.88 mg |
| Magnesium Stearate | 1.94 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 1.94 mg. An acceptable range is about 1.55 to about 2.33 mg.

The stock granulation of Part 5A and the Example 5 tablets were prepared according to the following procedures.

B. Stock Granulation Procedure

1. Deaggregate dapagliflozin propylene glycol hydrate and magnesium stearate separately using a suitable screen.
2. Mix microcrystalline cellulose, dapagliflozin propylene glycol hydrate, portion of crospovidone, portion of croscarmellose sodium, portion of silicon dioxide and anhydrous lactose in a suitable blender.
3. Add talc and intragranular magnesium stearate to the mixture from Step 2 and mix in a suitable blender.
4. Compact the powder blend from Step 3.
5. Reduce compact from Step 4 to form granules.
6. Mix the granules from Step 5 with remaining amounts of crospovidone, croscarmellose sodium and silicon dioxide.
7. Mix the granules from Step 6 with remaining amount of magnesium stearate.

C. Example 5—Product: Dapagliflozin/Dapagliflozin-PGS Tablet, 10 mg

1. Setup the tabletting equipment.
2. Compress the Example 5 stock granulation into tablets.

Example 6

Preparation of Dapagliflozin/Dapagliflozin-PGS Tablet, 50 mg Product:
Dapagliflozin/Dapagliflozin-PGS Tablet, 50 mg A. Tablet Composition

| Ingredient | Amount |
| --- | --- |
| Dapagliflozin propylene glycol hydrate (Or equivalent amount of Dapagliflozin) | 61.66 mg |
| Microcrystalline Cellulose | 114.09 mg |
| Anhydrous Lactose | 62.60 mg |
| Crospovidone | 21.91 mg |
| Croscarmellose Sodium | 9.39 mg |
| Talc | 31.30 mg |
| Silicon Dioxide | 7.20 mg |
| Magnesium Stearate | 4.85 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used.

The target amount of magnesium stearate is 4.85 mg. An acceptable range is about 3.76 to about 5.95 mg.

The stock granulation of Part 6A and the Example 6 tablets were prepared according to the following procedures.

B. Stock Granulation Procedure

1. Mix dapagliflozin propylene glycol hydrate, microcrystalline cellulose, anhydrous lactose, crospovidone, croscarmellose sodium, talc and silicon dioxide in a suitable blender.
2. Pass the mixture from Step 1 through a suitable mill.
3. Determine the yield from Step 1 and calculate the amount of magnesium stearate required.
4. Mix the mixture from Step 2 in a suitable blender.
5. Mix the mixture from Step 4 with magnesium stearate.
6. Dry granulate the powder blend from Step 5.
7. Size the granulation from Step 6.
8. Determine the yield based on Step 7.
9. Mix the granules from Step 8 with remaining amount of crospovidone, croscarmellose sodium and silicon dioxide.
10. Mix the granules from Step 9 with remaining amount of magnesium stearate.

C. Example 6 Product: Dapagliflozin/Dapagliflozin-PGS Tablet, 50 mg

1. Setup the tabletting equipment.
2. Compress the Example 6 stock granulation into tablets.

The so-formed tablets of Example 4 (2.5 mg), Example 5 (10 mg) and Example 6 (50 mg) are used to treat obesity.

Example 7

Treatment of Metabolic Disorders

An oral solution (0.5 mg/mL) was prepared by dissolving the dapagliflozin or dapagliflozin-PGS in a mixture of polyethylene glycol 400, NF and water (USP or purified water) 30:70% v/v. The oral solution was clear and colorless.

Figure 2:
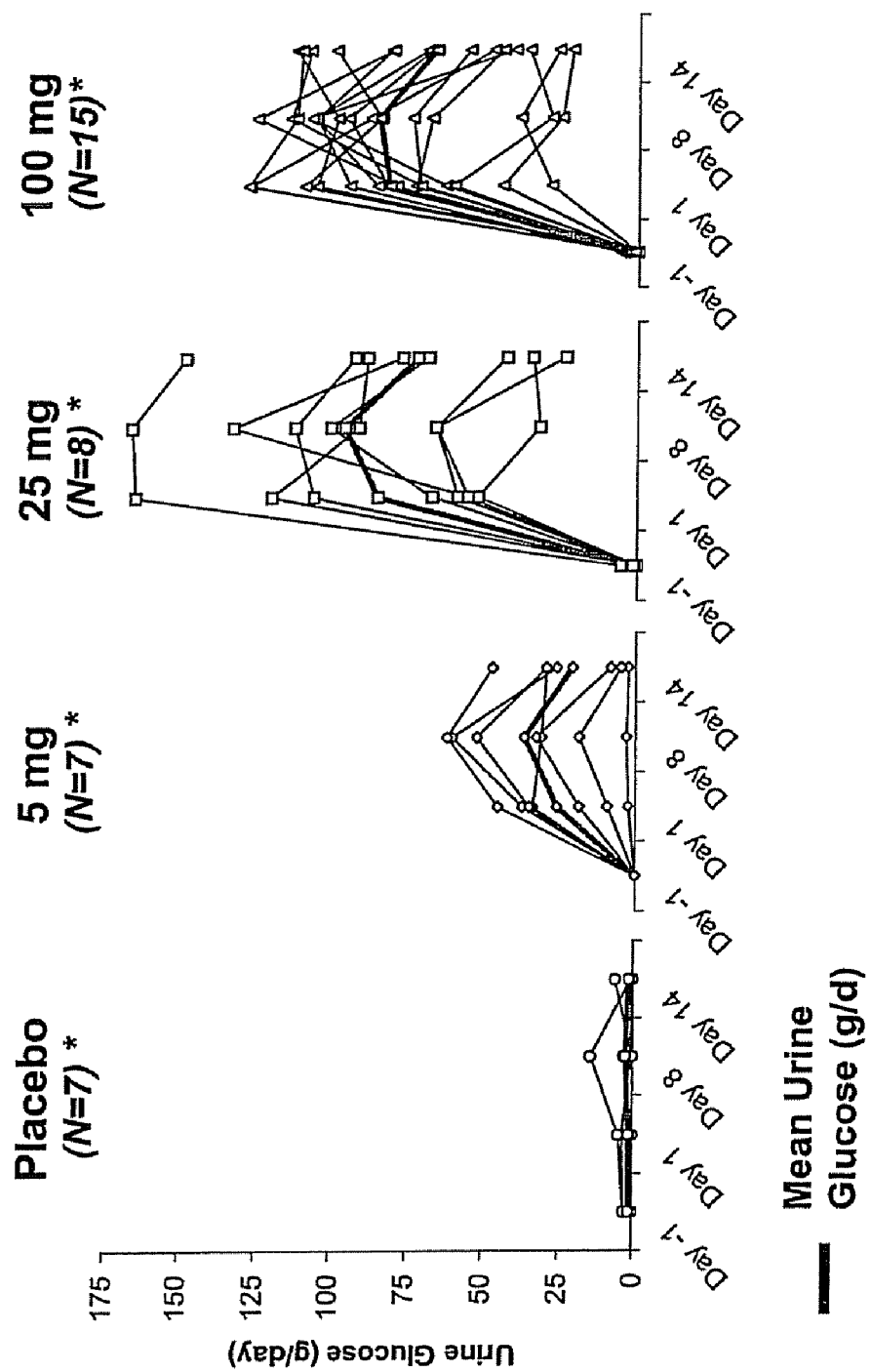
FIG. 2 depicts a series of graphs showing urine glucose excretion in diabetic subjects treated with Dapagliflozin-PGS and placebo.

The glucosuric effects of dapagliflozin PGS results in significant loss of calories in the urine versus a known SGLT2 inhibitor (GSK 869,682). The results of an indirect comparison of two single ascending dose studies of SGLT2 inhibitors is shown in FIG. 1. The top panel in FIG. 1 shows the amount of glucose excretion/day in healthy subjects taking 50, 100, 200 or 500 mg of GSK 869,682. The bottom panel in FIG. 1 shows the amount of glucose excretion/day in healthy subjects taking 5, 20, 50 or 100 mg of dapagliflozin PGS. This is further confirmed in a 14-day multiple ascending dose phase 2a study in subjects with type 2 diabetes. Results from the 24-hour glucose excretion are shown in FIG. 2. The mean urine glucose is shown in the bolded lines. Patients with type 2 diabetes were treated with placebo, 5 mg dapagliflozin propylene glycol, 25 mg dapagliflozin propylene glycol, or 100 mg dapagliflozin propylene glycol. Results from the 24-hour glucose excretion show that subjects taking 5 mg, 25 mg, and 100 mg dapagliflozin propylene glycol had significantly higher urine glucose excretion compared to subjects taking placebo.

Diet-Induced Obesity in Rats

Obesity was induced in male Sprague-Dawley rats (mean baseline weight=220 g) via ad libitum access to 2 diets: normal diet (Harlan Teklad rat chow; 3.5 kcal/gm, 5% vegetable fat) and high-sucrose/high-fat diet (Research Diets D12327; 4.6 kcal/gm, 40% sucrose and 40% vegetable fat). Rats under these conditions typically consume approximately 30 g/day of the high-sucrose/high-fat chow and 2 g/day of the normal Harlan Teklad rat chow. A 220-g rat given access to both diets will weigh approximately 750 g after 10 weeks.

Acute Glucosuria Study

Figure 3:
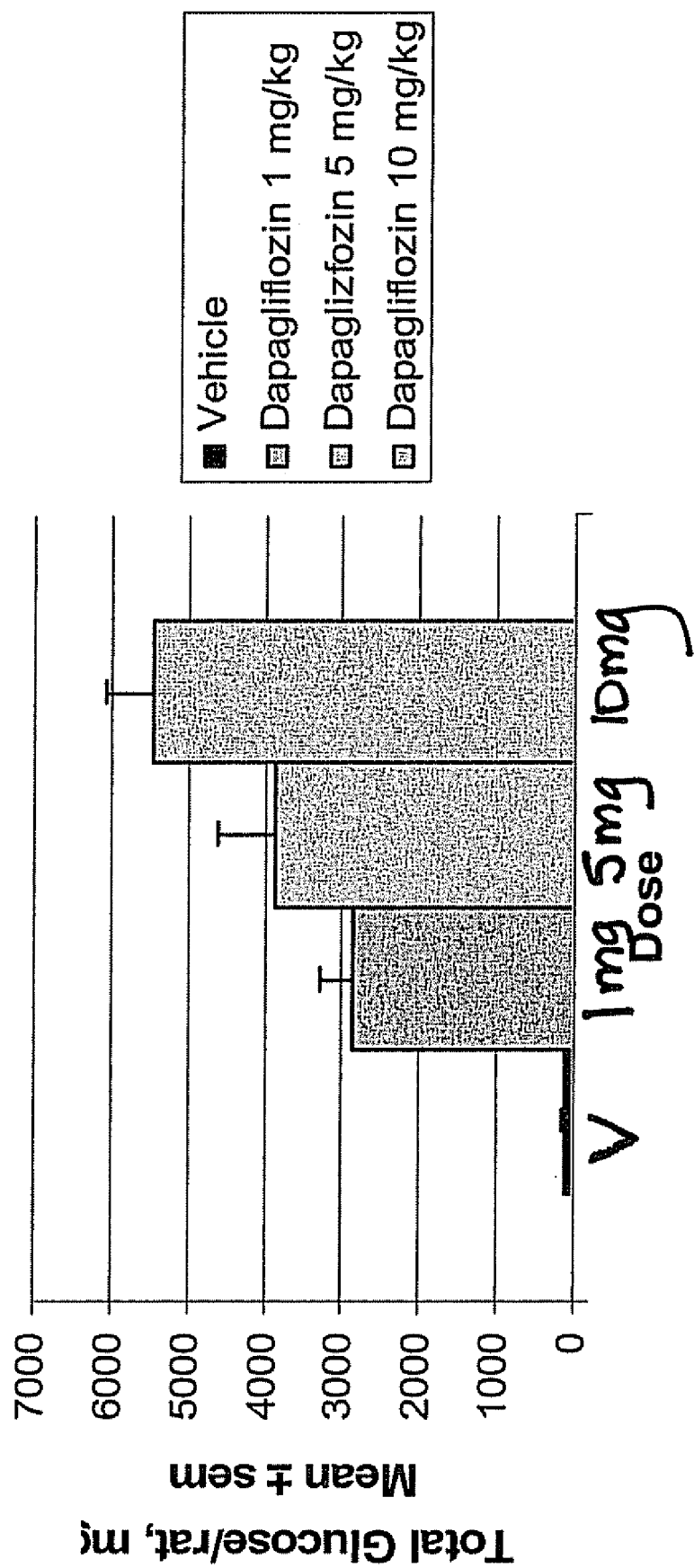
FIG. 3 depicts glucosuria in diet induced obese rats treated with Dapagliflozin-PGS.

Dapagliflozin PGS (1, 5, or 10 mg/kg) or placebo (vehicle) was orally administered to diet-induced obese (DIO) rats after 24-hour baseline urine samples were collected. Urine volume and glucose concentration were used to determine total urine glucose loss over 24 hours post dose. Total urine glucose was determined after 24 hours administration of dapagliflozin propylene glycol. Total glucose lost was calculated as volume of urine×glucose concentration. The results in FIG. 3 show that the total amount of glucose lost over 24 hours post dose was significantly increased with increasing doses of dapagliflozin propylene glycol in a dose-dependent manner.

Chronic Weight Loss Study

DIO rats were sorted into treatment groups based on body weight, total kilocalories consumed, and body composition (via echo MRI). Dapagliflozin PGS (0.5, 1 and 5 mpk) or placebo was orally administered to DIO rats for 28 days. To assess the importance of compensatory over-eating in drug-treated animals, a subgroup of rats that received 5 mg/kg of dapagliflozin was restricted to the food intake of the placebo group. Body weight and the weight of both diets were determined daily. Respiratory quotient data were obtained on days 2 and 15 of the study, echo MRI was obtained on day 22, and blood was collected for a fasting clinical chemistry tests on day 27.

Figure 4:
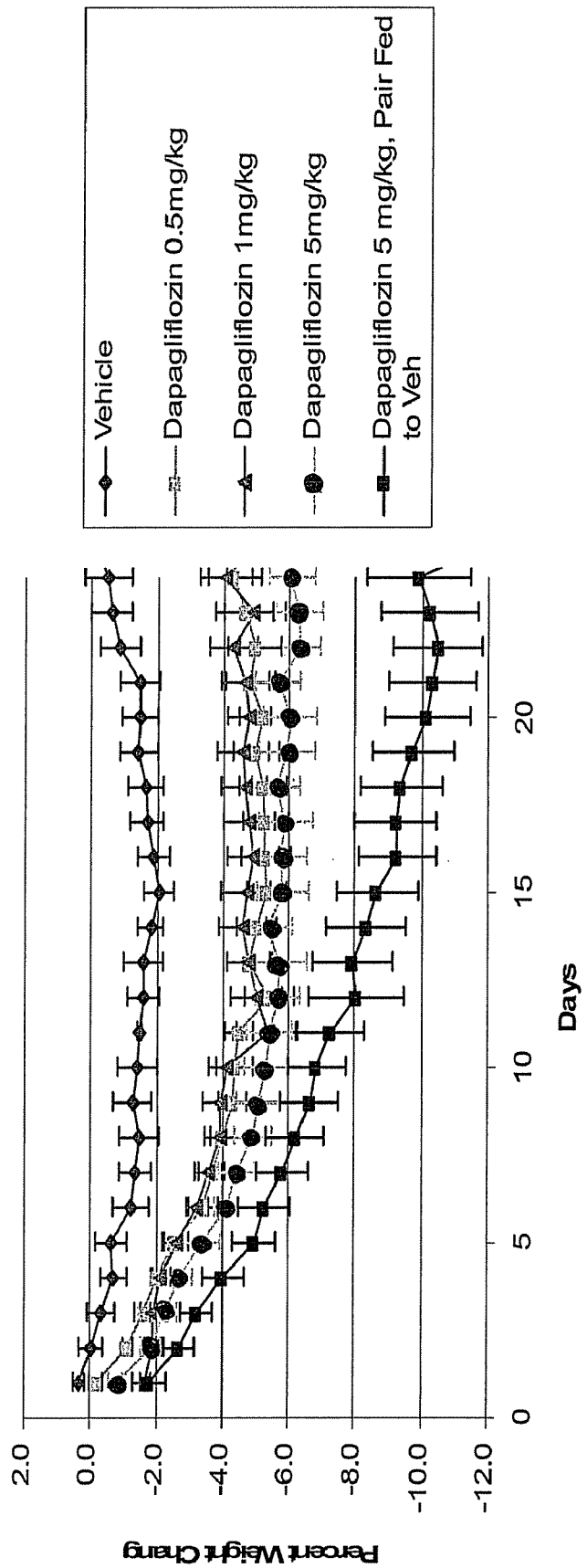
FIG. 4 depicts weight loss in diet-induced obese rats treated with Dapagliflozin-PGS.

As shown in FIG. 4, chronically administered dapagliflozin propylene glycol (administered daily over 25 days) produced significant weight loss ($p<0.05$ versus vehicle) in diet-induced obese rats. If the compound-induced overeating was prevented (dapagliflozin propylene glycol mg/kg pair fed to vehicle group), then the weight loss was greater. Percent weight changes were calculated as daily weight−day 0 weight×100.

The weight loss study with Compound IIIA (0.1, 0.3, 1, and 3 mg/kg) was performed using the same methods as the Dapagliflozin study. As shown in FIG. 5, chronically administered Compound IIIA (administered daily over 25 days) produced significant weight loss in diet-induced obese rats in a dose proportional manner.

Weight Loss in Type II Diabetic Patients

Treatment naive type II diabetes mellitus patients, n=389, with inadequate blood glycemic control and low mean glucosuria at baseline were given once-daily oral treatments with dapagliflozin (2.5, 5, 10, 20, or 50 mgs), metformin XR® (750 mg titrated to 1500 mgs), or placebo over 12-weeks.

Treatment with dapagliflozin-PGS resulted in consistent and sustained increases in urinary glucose excretion, rising to mean glucosuria values between 51.8 g/day to 85.0 g/day at week 12 from baseline means between 5.8 grams/day to 10.9 grams/day. Mean glucosuria with placebo and metformin both remained low, 5.7 grams/day and 5.6 grams/day respectively at week 12. A higher proportion of patients in each of the dapagliflozin-PGS groups achieved a 5% weight reduction than those taking placebo. Mean percent reductions for body weight and absolute changes in body mass index (BMI) over 12 weeks are shown in Table III.

TABLE III

| | Dapagliflozin-PGS Dose | | | | | | |
|---|---|---|---|---|---|---|---|
| | 2.5 mgs n = 59 | 5 mgs n = 58 | 10 mgs n = 47 | 20 mgs n = 59 | 50 mgs n = 56 | Placebo n = 54 | Metformin n = 56 |
| Baseline weight (kg) | 90 | 89 | 86 | 88 | 91 | 89 | 88 |
| Mean reduction in weight (%) | −2.7 | −2.5 | −2.7 | −3.4 | −3.4 | −1.2 | −1.7 |
| Baseline BMI (kg/m$^2$) | 31 | 31 | 30 | 31 | 32 | 32 | 32 |
| Mean reduction in BMI | −0.9 | −0.8 | −0.8 | −1.0 | −1.1 | −0.3 | −0.5 |

What is claimed is:

1. A method for treating obesity in a mammalian subject or patient comprising administering to a mammalian subject or patient in need of such treatment a therapeutically effective amount of an SGLT2 inhibitor having the structure

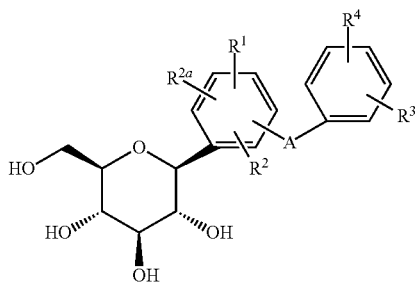

wherein $R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which can contain 1 to 4 heteroatoms in the ring which are N, O, S, SO, and/or $SO_2$;

$R^3$ and $R^4$ are independently hydrogen, OH, $OR^{5a}$, OAryl, $OCH_2Aryl$, alkyl, cycloalkyl, $CF_3$, —$OCHF_2$, —$OCF_3$, halogen, —CN, —$CO_2R^{5b}$, —$CO_2H$, $COR^{6b}$, —$CH(OH)R^{6c}$, —$CH(OR^{5h})R^{6d}$, —$CONR^6R^{6a}$, —$NHCOR^{5c}$, —$NHSO_2R^{5d}$, —$NHSO_2Aryl$, Aryl, —$SR^{5e}$, —$SOR^{5f}$, —$SO_2R^{5g}$, —$SO_2Aryl$, or a five, six or seven membered heterocycle which can contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which can contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$, and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which can contain 1 to 4 heteroatoms in the ring which are N, O, S, SO, and/or $SO_2$;

A is O, S, NH, or $(CH_2)_n$ where n is 0-3, or a pharmaceutically acceptable salt, stereoisomer, or prodrug ester thereof;

with the proviso that where A is $(CH_2)_n$ where n is 0, 1, 2, or 3 or A is O, and at least one of $R^1$, $R^2$, and $R^{2a}$ is OH or $OR^5$, then at least one of $R^1$, $R^2$, and $R^{2a}$ is $CF_3$, $OCF_3$, or $OCHF_2$ and/or at least one of $R^3$ and $R^4$ is $CF_3$, —$OCHF_2$, —$OCF_3$, —CN, —$CO_2R^{5b}$, $CH(OR^{5h})R^{6d}$, $CH(OH)R^{6c}$, $COR^{6b}$, —$NHCOR^{5c}$, —$NHSO_2R^{5d}$, —$NHSO_2Aryl$, Aryl, —$SR^{5e}$, —$SOR^{5f}$, —$SO_2R^{5g}$ or —$SO_2Aryl$, wherein the amount of the SGLT2 inhibitor does not cause a significant reduction in blood glucose levels in the mammalian subject or patient and does not cause hypoglycemia in the in the mammalian subject or patient.

2. The method according to claim 1, wherein the mammal is a human.

3. The method according to claim 1, wherein the mammal is a human with type II diabetes mellitus.

4. The method according to claim 1, wherein the SGLT2 inhibitor has the structure

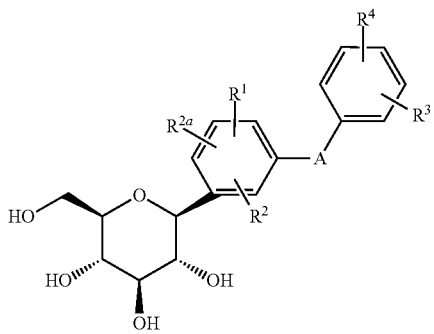

wherein

A is $CH_2$; $R^1$ is hydrogen, halogen or lower alkyl; $R^2$ and $R^{2a}$ are each H; $R^3$ is H; $R^4$ is lower alkyl, —$COR^{6b}$, —$CH(OH)R^{6c}$, —$CH(OR^{5h})R^{6d}$, $R^{5a}O$, —$OCHF_2$, —$OCF_3$ or —$SR^{5e}$.

5. The method according to claim 1, wherein the SGLT2 inhibitor has the structure

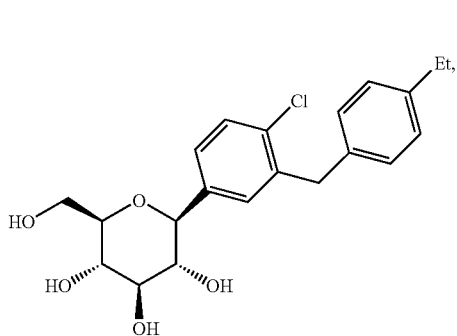

or a pharmaceutically acceptable salt thereof, a stereoisomer thereof, or a prodrug ester thereof.

6. The method according to claim 1, wherein the SGLT2 inhibitor has the structure

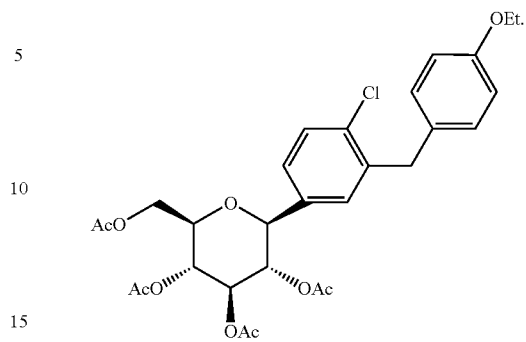

7. The method according to claim 1, wherein the SGLT2 inhibitor is dapagliflozin provided as a propylene glycol hydrate.

* * * * *